(12) United States Patent
Giesing

(10) Patent No.: US 10,857,173 B2
(45) Date of Patent: Dec. 8, 2020

(54) METHODS OF TREATING TUMOR METASTASIS

(71) Applicant: TARIS BIOMEDICAL LLC, Lexington, MA (US)

(72) Inventor: Dennis Giesing, Lee's Summit, MO (US)

(73) Assignee: TARIS Biomedical LLC, Lexington, MA (US)

( * ) Notice: Subject to any disclaimer, the term of this patent is extended or adjusted under 35 U.S.C. 154(b) by 15 days.

(21) Appl. No.: 16/045,586

(22) Filed: Jul. 25, 2018

(65) Prior Publication Data

US 2019/0060344 A1 Feb. 28, 2019

Related U.S. Application Data

(60) Provisional application No. 62/536,949, filed on Jul. 25, 2017.

(51) Int. Cl.
*A61K 31/7068* (2006.01)
*A61P 35/00* (2006.01)
*A61K 9/00* (2006.01)

(52) U.S. Cl.
CPC ........ *A61K 31/7068* (2013.01); *A61K 9/0004* (2013.01); *A61K 9/0034* (2013.01); *A61P 35/00* (2018.01)

(58) Field of Classification Search
CPC .............. A61K 31/7068; A61K 9/0034; A61K 9/0004; A61P 35/00
See application file for complete search history.

(56) References Cited

U.S. PATENT DOCUMENTS

| | | |
|---|---|---|
| 8,343,516 B2 | 1/2013 | Daniel et al. |
| 8,679,094 B2 | 3/2014 | Cima et al. |
| 9,636,488 B2 | 5/2017 | Giesing |
| 10,543,346 B2 | 1/2020 | Giesing |
| 2008/0221557 A1 | 9/2008 | Santini et al. |
| 2010/0331770 A1 | 12/2010 | Lee et al. |
| 2012/0203203 A1 | 8/2012 | Lee et al. |
| 2013/0158675 A1 | 6/2013 | Hutchins, III et al. |
| 2014/0056986 A1 | 2/2014 | Desai |
| 2014/0221981 A1 | 8/2014 | Cima |
| 2014/0276636 A1 | 9/2014 | Lee et al. |
| 2015/0165177 A1 | 6/2015 | Giesing |
| 2015/0165178 A1 | 6/2015 | Giesing |
| 2015/0216937 A1 | 8/2015 | Wen |
| 2015/0250717 A1 | 9/2015 | Giesing |
| 2015/0360012 A1 | 12/2015 | Sansone et al. |
| 2016/0008271 A1 | 1/2016 | Lee |
| 2016/0199544 A1 | 7/2016 | Lee et al. |
| 2016/0310715 A1 | 10/2016 | Lee |
| 2017/0157360 A1 | 6/2017 | Cima et al. |
| 2019/0175637 A1 | 6/2019 | Giesing |
| 2019/0388338 A1 | 12/2019 | Giesing |
| 2020/0060966 A1 | 2/2020 | Giesing |

FOREIGN PATENT DOCUMENTS

| | | |
|---|---|---|
| WO | WO-2011/031855 A2 | 3/2011 |
| WO | WO-2011/031855 A3 | 3/2011 |
| WO | WO-2014/036556 A2 | 3/2014 |
| WO | WO-2014/144066 A1 | 9/2014 |
| WO | WO-2014/145638 A1 | 9/2014 |
| WO | WO-2015/026813 A1 | 2/2015 |
| WO | WO-2015/134911 A1 | 9/2015 |
| WO | WO-2015/200752 A1 | 12/2015 |
| WO | WO-2017/193098 A1 | 11/2017 |
| WO | WO2017193098 A1 | 11/2017 |
| WO | WO2019094517 A1 | 5/2019 |
| WO | WO2020028554 A1 | 2/2020 |

OTHER PUBLICATIONS

Vogelzang et al., Urology, 1999, 53, p. 243-250. (Year: 1999).*
Stadler et al., Journal of Clinical Oncology, 1997, 15(11), p. 3394-3398. (Year: 1997).*
Clinicaltrials.gov Archive—NCT02720367. (Feb. 25, 2016; last updated on Oct. 18, 2016). "A Phase 1b, Multicenter, Open Label Study Evaluating Safety, Tolerability and Preliminary Efficacy of GemRIS 225 mg in Subjects With Non-Muscle-Invasive Urothelial Carcinoma of the Bladder," Taris Biomedical LLC, located at <https://clinicaltrials.gov/ct2/history/NCT02720367?V_5= View#StudyPageTop>, last visited on Nov. 8, 2018, 9 pages.
Clinicaltrials.gov Archive—NCT02722538. (Mar. 29, 2016; last updated on Oct. 18, 2016). "A Phase 1b, Multicenter, Open Label Study Evaluating Safety, Tolerability and Preliminary Efficacy of GemRIS 225 mg in Subjects With Muscle-Invasive Transitional Cell Carcinoma of the Bladder," Taris Biomedical LLC, located at <https://clinicaltrials.gov/ct2/history/NCT02722538?V_9= View#StudyPageTop> last visited on Nov. 8, 2018, 12 pages.
International Search Report and Written Opinion of the International Searching Authority dated Sep. 17, 2018 for PCT Application No. PCT/US2018/043770, filed on Jul. 25, 2018, twelve pages.
"TARIS Biomedical Announces Positive Results from Ph1b Trial of TAR-200 (GemRIS™) in Patients with Muscle Invasive Bladder Cancer," retrieved from URL:https://www.businesswire.com/news/home/20170106005117/en/TARIS-Biomedical-Announces-Positive-Results-Phlb-Trial, last visited Nov. 6, 2019), (Jan. 6, 2017), 3 pages.
Bidnur, S. et al. (Jan. 7, 2016). "Inhibiting Immune Checkpoints for the Treatment of Bladder Cancer," Bladder Cancer 2(1):15-25.

(Continued)

*Primary Examiner* — Jonathan S Lau

(74) *Attorney, Agent, or Firm* — Morrison & Foerster LLP

(57) ABSTRACT

The present invention provides methods for treating or suppressing tumor metastasis at a site distinct from the bladder in an individual having a urothelial carcinoma of lower tract, comprising locally delivering to the bladder an effective amount of a chemotherapeutic agent (such as gemcitabine), wherein the chemotherapeutic agent is delivered continuously to the bladder for a sustained period of time (such as at least 24 hours).

41 Claims, 12 Drawing Sheets

(56) References Cited

OTHER PUBLICATIONS

Clinicaltrials.gov. NCT03404791. (Jan. 19, 2018). "Safety and Tolerability of TAR-200 in Subjects With Muscle-Invasive Bladder Cancer Who Are Unfit for Radical Cystectomy," located at https://www.clinicaltrials.gov/ct2/history/NCT03404791?V_1=View , last visited on Feb. 21, 2019, 15 pages.
Cockerill, P.A. et al. (Mar. 2016; e-pub May 2, 2015.). "Intravesical Gemcitabine in Combination with Mitomycin C as Salvage Treatment in Recurrent Non-Muscle-Invasive Bladder Cancer," BJU Int. 117(3):456-462.
Daneshmand, S. et al. (2017; e-pub. May 30, 2017). "Effect of GemRIS (Gemcitabine-Releasing Intravesical System, TAR-200) on Antitumor Activity in Muscle-Invasive Bladder Cancer (MIBC)," Journal of Clinical Oncology 35(15):suppl. e16000, located at, http://ascopubs.org/doi/abs/10.1200/JCO.2017.35.15_suppl.e16000, last visited on Feb. 21, 2019, 2 pages.
International Preliminary Report on Patentability, dated Jan. 28, 2020, for PCT Application No. PCT/US2018/043770, filed Jul. 25, 2018, twelve pages.
Leach, D.R. et al. (Mar. 22, 1996). "Enhancement of Antitumor Immunity by CTLA-4 Blockade," Science 271(5256)1734-1736.
Li, J. et al. (Oct. 2014). Effect of Internal Iliac Artery Chemotherapy after Transurethral Resection of Bladder Tumor for Muscle Invasive Bladder Cancer, Chin J Cancer Res. 26(5):558-563.
Lorenzo, G.D. et al. (Apr. 15, 2010). "Genncitabine Versus Bacille Calmette-Guerin After Initial Bacille Calmette-Gue'rin Failure in Non-Muscle-Invasive Bladder Cancer,". Cancer 116:1893-1900.
Mertens, L.S. et al. (Oct. 2012). "Carboplatin Based Induction Chemotherapy for Nonorgan Confined Bladder Cancer-A Reasonable Alternative for Cisplatin Unfit Patients?" Journal of Urology 188:1108-1114.
Oh, K.S. et al. (Nov. 2, 2009). "Combined-Modality Therapy With Gemcitabine and Radiation Therapy as a Bladder Preservation Strategy: Long-Term Results of a Phase I Trial," International Journal of Radiation: Oncology Biology Physics 74(2):511-517.
Pardoll, D.M. (2012). "The Blockade of Immune Checkpoints in Cancer Immunotherapy," Nat. Rev. Cancer 12(4):252-264.
Shariat, S.F. et al. (May 2010). "Update on Intravesical Agents for Non-Muscle-Invasive Bladder Cancer," Immunotherapy 2(3):381-392, 19 pages.
Shelley, M.D. et al. (Feb. 2012). "Intravesical Gemcitabine Therapy for Non-Muscle Invasive Bladder Cancer (NMIBC): A Systematic Review," BJU International 109(4):496-505.
Skinner, E.C. et al. (Oct. 2013; e-pub. Apr. 15, 2013). "SWOG S0353: Phase II Trial of Intravesical Gemcitabine in Patients with Nonmuscle Invasive Bladder Cancer and Recurrence after 2 Prior Courses of Intravesical Bacillus Calmette-Guérin," The Journal of Urology 190(4):1200-1204, 11 pages.
Sternberg, I.A. et al. (Nov. 2013). "Intravesical Gemcitabine for High Risk, Nonmuscle Invasive Balder Cancer After Bacillus Calmette-Guerin Treatment Failure," Journal of Urology 190(5):1686-1691.
Wolchok, J.D. et al. (2008). "The Mechanism of Anti-CTLA-4 Activity and the Negative Regulation of T-Cell Activation," The Oncologist 13(Suppl 4):2-9.
Yuh, B.E. et al. (May 2013). "Pooled Analysis of Clinical Outcomes with Neoadjuvant Cisplatin and Gemcitabine Chemotherapy for Muscle Invasive Bladder Cancer," Journal of Urology 189:1682-1686.
Breyer, B.N. et al. (2010). "Sequential Intravesical Gemcitabine and Mitomycin C Chemotherapy Regimen in Patients With Non-Muscle Invasive Bladder Cancer," Urol. Oncol. 28(5):510-514. 9 pages.
Dall'Era, M.A. et al. (Jul. 2012). "Contemporary Management of Muscle-Invasive Bladder Cancer," Expert Rev. Anticancer Ther. 12(7):941-950, 18 pages.

\* cited by examiner

FIG. 1  Bladder Cannulation & Perfusion System, Location of Tumors

METHODS OF TREATING TUMOR METASTASIS

CROSS-REFERENCE TO RELATED APPLICATION

This application claims priority benefit of U.S. Provisional Application No. 62/536,949, filed on Jul. 25, 2017, entitled "METHODS OF TREATING TUMOR METASTASIS," the contents of which this incorporated herein by reference in its entirety.

TECHNICAL FIELD

The present invention relates to methods of treating tumors or tumor metastasis at a distant site, by continuously delivering to the bladder an effective amount of a chemotherapeutic agent.

BACKGROUND

Cancerous diseases and tumors in general are among the major causes for human deaths and severe illness. Tumor metastasis is a major contributor to the deaths of cancer patients. Even after surgical removal of a tumor, patients frequently suffer from cancer, mostly from tumor metastasis.

Metastatic cancer is especially difficult to treat because the metastatic tumor cells can adapt quickly and become resistant to treatment. Typically, metastatic cancer requires systemic therapy to reach cancer cells throughout the body, such as chemotherapy or hormone therapy. Effectiveness of these therapies depends on various factors such as the type of the specific cancer and specific patient population. In general, effectiveness of currently available therapies for metastatic cancer is far from ideal because of the poor effectiveness and serious and/or unnecessary damage to the human body.

Bladder cancer is a significant medical problem, and currently available treatment options are unsatisfactory for a number of reasons. In general, bladder cancers are classified as muscle invasive bladder cancer (MIBC) or non-muscle invasive bladder cancer (NMIBC). The pathological classification and staging of bladder cancer is as follows: pTa (urothelial involvement); pTis (high risk urothelial confined); pT1 (lamina propria invasion); pT2 (muscularis invasion); pT3 (perivesical fat invasion); and pT4 (pelvic organ extension). Bladder cancers can also be classified by grade as Grade 1/3 (well differentiated); Grade 2/3 (moderately differentiated); and Grade 3/3 (poorly differentiated). Recently the World Health Organization recommended using a two scale grading system for bladder cancer, low grade and high grade. In addition, bladder cancers can be classified by stage as Stages 0-IV. Most bladder cancers are transitional cell carcinomas of epithelial origin and classified as non-muscle invasive bladder cancer (NMIBC) confined to the inner lining of the bladder. At initial presentation, most bladder cancers are superficial NMIBCs and include stages pTa, pTis and pT1 disease. Muscle invasive bladder cancer (MIBC) includes stages pT2, pT3 and pT4.

The typical clinical approach used to treat early stage NMIBC is cystoscopic visualization followed by surgical removal of the tumor(s), known as transurethral resection (TUR). However, there is a high rate of recurrence after surgery and the cancer may progress to muscle-invasive disease. Therefore, surgery is often combined with adjuvant intravesical instillation (direct delivery of the chemotherapeutic agent into the bladder through a urinary catheter for a brief period of time usually less than 1 hour) of chemotherapeutic or immunotherapeutic agents to help suppress or delay the recurrence. Bacillus Calmette-Guerin (BCG) is such an immunotherapeutic and is instilled into the bladder following surgery for higher grades of non-muscle invasive bladder cancer (NMIBC). However, many patients do not respond to BCG, and BCG treatment can also induce a range of adverse effects leading to discontinuation of treatment. Chemotherapeutic agents are usually reserved for patients who have failed BCG therapy. Chemotherapy is typically applied intravesically to concentrate the chemotherapeutic agent at the tumor sites to help eliminate any residual tumor after resection while reducing systemic exposure of the drug.

Muscle invasive bladder cancer is generally more likely to metastasize compared to non-muscle invasive bladder cancer. Accordingly, patients with muscle invasive bladder cancer typically receive cisplatin-based neoadjuvant chemotherapy followed by radical cystectomy, or removal of the bladder. On the other hand, patients with muscle-invasive bladder cancer who are medically unfit, or elect not to have a radical cystectomy typically receive maximal transurethral resection of bladder tumors (TURBT) in combination with chemotherapy.

One such chemotherapeutic agent used in clinical trials for treating bladder cancer is gemcitabine. Gemcitabine (2',2'-difluorodeoxycytidine) is a pyrimidine analogue with activity against metastatic bladder cancer. Gemcitabine has also been used in clinical trials to treat NMIBC by instillation in the bladder with various weekly schedules. Gemcitabine is typically instilled over 1 to 2 hours once or twice a week for several weeks at doses typically ranging from 500 to 2000 mg in up to 100 mL of saline.

It is known that such liquid formulations are voided from the bladder after short dwell times of 1 to 2 hours thus limiting their therapeutic benefit. In addition, high concentrations (40 mg/mL) and high doses (up to 2 grams per instillation) are used in an attempt to achieve therapeutic tissue levels with limited dwell time. However, in addition to local tolerability issues, intravesical delivery of high doses of gemcitabine can lead to significant systemic absorption and cause gastrointestinal, bladder and bone marrow toxicity further limiting its utility.

Systemic gemcitabine is often used in combination with systemic cisplatin both neoadjuvantly and adjuvantly to radical cystectomy to treat muscle invasive bladder cancer and to treat metastatic disease. However, many patients are ineligible or refuse treatment with these agents due to their side effects which include bone marrow suppression.

Accordingly, there remains a need for methods for treating tumors at distant sites in an individual with a tumor in the bladder.

The disclosures of all publications, patents, patent applications and published patent applications referred to herein are hereby incorporated herein by reference in their entirety.

BRIEF DESCRIPTION

The present invention in various aspects provides methods of treating tumor metastasis, reducing (such as eradicating) preexisting tumor metastasis, reducing incidence or burden of preexisting tumor metastasis, suppressing or delaying tumor metastasis, inhibiting tumor cells at a second site distinct from a first tumor site in the bladder of an individual comprising locally delivering to the bladder an effective amount of a chemotherapeutic agent, wherein the chemotherapeutic agent is delivered continuously to the bladder for period of time.

In some embodiments, there is provided a method of inhibiting tumor cell growth at a second tumor site distinct from a first tumor site in the bladder of an individual, comprising locally delivering to the bladder an effective amount of a chemotherapeutic agent, wherein the chemotherapeutic agent is delivered continuously to the bladder for at least about 24 hours. In some embodiments, the tumor cells at the second tumor site are located at a pelvic node. In some embodiments, the tumor cells at the second tumor site are located at a distant node. In some embodiments, the tumor cells at the second tumor site are circulating tumor cells. In some embodiments, the tumor cells at the first tumor site result from metastasis of a primary tumor at the second tumor site. In some embodiments, the tumor cells at the second site are selected from the group consisting of liver, lung, bone, brain, lymph node, pelvic node, peritoneum, skin, prostate, breast, colon, rectum, and cervix. In some embodiments, the individual has a urothelial carcinoma of lower tract.

In some embodiments, also provided herein is a method of treating or suppressing tumor metastasis at a site distinct from the bladder in an individual having a urothelial carcinoma of lower tract, comprising locally delivering to the bladder an effective amount of a chemotherapeutic agent, wherein the chemotherapeutic agent is delivered continuously to the bladder for at least about 24 hours. In some embodiments, the tumor metastatic site is at one or more of: liver, lung, bone, brain, lymph node, pelvic node, peritoneum, skin, prostate, breast, colon, rectum, and cervix. In some embodiments, the tumor metastasis is at two or more different sites.

In some embodiments according to any of the methods described above, the individual has bladder cancer. In some embodiments, the individual has muscle invasive bladder cancer or carcinoma in situ (CIS). In some embodiments, the individual is unfit for or refuses cystectomy.

In some embodiments according to any of the methods described above, the individual has not undergone transurethral resection of bladder tumors (TURBT).

In other embodiments, the individual has undergone transurethral resection of bladder tumors (TURBT). In some of these embodiments, the individual has undergone transurethral resection of bladder tumors (TURBT) and has residual tumor at the site of resection.

In some embodiments according to any of the methods described above, the chemotherapeutic agent is delivered at a dose of from about 1 mg/day to about 300 mg/day. In some embodiments, the concentration of the chemotherapeutic agent in the urine is from about 0.1 µg/mL to about 200 µg/mL during the delivery period.

In some embodiments according to any of the methods described above, the chemotherapeutic agent is delivered continuously to the bladder of the individual for a period of about 7 days to about three weeks. In some embodiments, the method comprises an induction delivery period followed by a maintenance delivery period. In some embodiments, the induction delivery period and the maintenance delivery period are separated by a rest period of about 7 to about 14 days. In some embodiments, the chemotherapeutic agent is delivered at a first release rate during the induction delivery period followed and a second release rate during the maintenance delivery period.

In some embodiments according to any of the methods described above, the method comprises a) an induction delivery period, wherein the concentration of chemotherapeutic agent in the urine of the individual is at least about 0.1 µg/mL; b) a rest period; and c) a maintenance delivery period, wherein the concentration of the chemotherapeutic agent in the urine of the individual is greater than about 0.1 µg/mL.

In some embodiments according to any of the methods described above, the individual does not receive a radiation therapy. In other embodiments, the method further comprises a radiation therapy.

In some embodiments according to any of the methods described above, the chemotherapeutic agent is delivered by an intravesical delivery device. In some embodiments, the intravesical device contains 100 mg to 500 mg of the chemotherapeutic agent. In some embodiments, the intravesical device comprises a housing configured for intravesical insertion; and a dosage form comprising chemotherapeutic agent, wherein the housing holds the dosage form and is configured to release chemotherapeutic agent. In some embodiments, the intravesical drug delivery device comprises: a housing defining a reservoir; a first unit contained within the reservoir, the first unit comprising an chemotherapeutic agent; and a second unit contained within the reservoir in a position distinct from the first unit, wherein the second unit comprises a functional agent that facilitates in vivo release of the chemotherapeutic agent from the housing. In some embodiments, the intravesical drug delivery device comprises a housing which contains and controllably releases the chemotherapeutic agent and is elastically deformable between a retention shape configured to retain the device in the individual's bladder and a deployment shape for passage of the device through the individual's urethra. In some embodiments, the device comprises a drug reservoir lumen bounded by a first wall and a second wall, wherein the first wall is impermeable to the drug and the second wall is permeable to the chemotherapeutic agent. In some embodiment, the chemotherapeutic agent is released from the device by osmotic pressure. In some embodiments, the chemotherapeutic agent is released from the device by diffusion. In some embodiment, the chemotherapeutic agent contained in the housing is in a non-liquid form. In some embodiments, the non-liquid form is selected from the group consisting of tablets, granules, powders, semisolids, capsules, and combinations thereof.

In some embodiments according to any of the methods described above, the chemotherapeutic agent is selected from the group consisting of a nucleoside analog, a taxane, a platinum-based agent, and an anthracycline analogue. In some embodiments, the chemotherapeutic agent is a nucleoside analog. In some of these embodiments, the nucleoside analog is gemcitabine.

In some embodiments according to any of the methods described above, the individual is human. In some embodiments, the individual is unsuitable for systemic chemotherapy. In some embodiments, the individual has a compromised immune system. In some embodiments, the individual has a high tumor burden.

BRIEF DESCRIPTION OF THE DRAWINGS

FIG. 5A is a plan view. FIG. 5B is a cross-sectional view taken along line 3-3 in FIG. 5A. FIG. 5C is a view of one end portion of the device disposed within the working channel of a deployment instrument, which is shown in partial cross-section.

DETAILED DESCRIPTION

Figure 1:
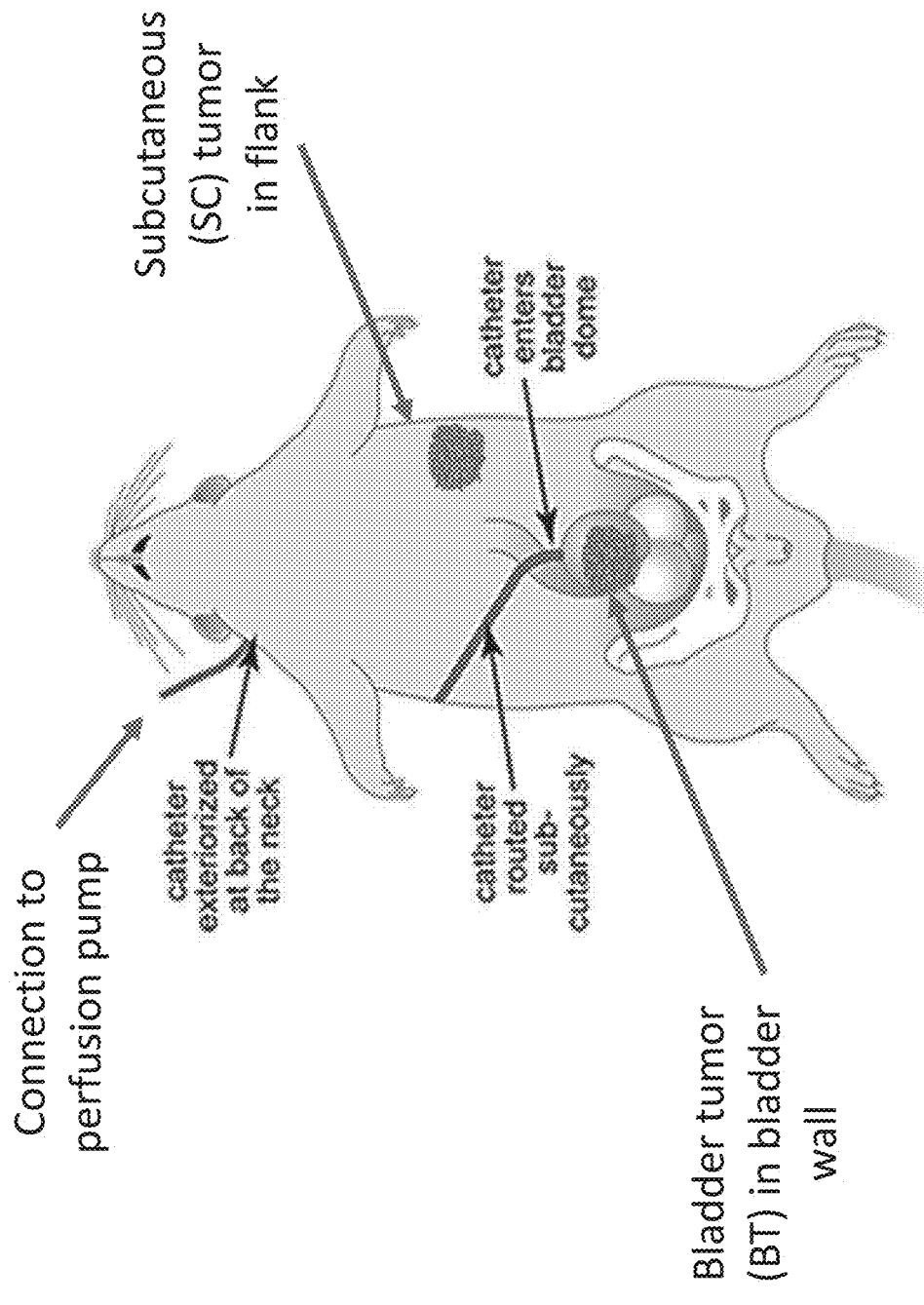
FIG. 1 shows a modified bladder perfusion system to introduce tumors into bladder and subcutaneous tissue.

The present application provides methods for treating or suppressing tumor metastasis at a site distinct from the bladder in an individual having bladder cancer, comprising locally delivering (such as intravesical) to the bladder an effective amount of a chemotherapeutic agent (such as gemcitabine). The application is based in part on the surprising finding that continuous delivery of gemcitabine to the bladder for a prolonged period of time has an extraordinary anti-tumor effect at a tumor site distinct from the bladder. The effect is even more pronounced when the gemcitabine is continuously delivered more than once. Therefore, continuous delivery of a chemotherapeutic agent (such as gemcitabine), especially a repeated local and continuous delivery of the chemotherapeutic agent (such as gemcitabine) to the bladder, as described herein, can be a robust method to treat or suppress tumor metastasis or treat non-bladder tumors, wherein the bladder is a primary tumor site or secondary or metastatic site.

Thus, the present invention in various aspects provides methods of treating tumor metastasis, reducing (such as eradicating) preexisting tumor metastasis, reducing incidence or burden of preexisting tumor metastasis, suppressing or delaying tumor metastasis, inhibiting tumor cells at a second site distinct from a first tumor site in the bladder of an individual comprising locally delivering to the bladder an effective amount of a chemotherapeutic agent, wherein the chemotherapeutic agent is delivered continuously to the bladder for period of time. In one aspect, there is provided a method of inhibiting tumor cell growth at a second tumor site distinct from a first tumor site in the bladder of an individual, comprising locally delivering to the bladder an effective amount of a chemotherapeutic agent, wherein the chemotherapeutic agent is delivered continuously to the bladder for at least about 24 hours. In another aspect, there is provided a method of treating or suppressing tumor metastasis at a site distinct from the bladder in an individual having a urothelial carcinoma of lower tract, comprising locally delivering to the bladder an effective amount of a chemotherapeutic agent, wherein the chemotherapeutic agent is delivered continuously to the bladder for at least about 24 hours. Also provided are kits for carrying out any methods described herein.

Definitions

As used herein, the singular forms "a," "an," and "the" include plural referents unless the context clearly dictates otherwise. For example, "a" or "an" means "at least one" or "one or more."

The term "continuous" or "continuously" as used herein refers to sustained administration of a chemotherapeutic agent (for example gemcitabine) over a sustained period of time.

The term "individual" as used herein refers to a mammal, including humans. An individual includes, but is not limited to, human, bovine, horse, feline, canine, rodent, or primate. In some embodiments, the individual is human.

Reference to "about" a value or parameter herein includes (and describes) embodiments that are directed to that value or parameter per se. For example, "about 7 days" includes 7 days.

The term "about X-Y" used herein has the same meaning as "about X to about Y."

The methods may be practiced in an adjuvant setting. "Adjuvant setting" refers to a clinical setting in which an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development/progression of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated. The methods provided herein may also be practiced in a neoadjuvant setting, i.e., the method may be carried out before the primary/definitive therapy. In some embodiments, the individual has previously been treated. In some embodiments, the individual has not previously been treated. In some embodiments, the treatment is a first line therapy.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), suppressing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer. The methods of the invention contemplate any one or more of these aspects of treatment.

The term "effective amount" used herein refers to an amount of a compound or composition sufficient to treat a specified disorder, condition or disease such as to ameliorate, palliate, lessen, and/or delay one or more of its symptoms. In reference to cancers, an effective amount comprises an amount sufficient to cause a tumor to shrink and/or to decrease the growth rate of the tumor (such as to suppress tumor growth) and/or to suppress, or delay other unwanted cell proliferation and/or to treat or suppress tumor metastasis and/or to reduce (such as eradiate) preexisting tumor metastasis and/or to reduce incidence or burden of preexisting tumor metastasis and/or to suppress or delay tumor metastasis and/or to inhibit tumor cells and/or to induce an immune response against a tumor cell. An effective amount can be administered in one or more administrations, for example, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) suppress or delay occurrence and/or recurrence of tumor; and/or (vii) relieve to some extent one or more of the symptoms associated with the cancer.

The term "nucleoside analog" is a nucleoside structurally similar to the naturally occurring residues in RNA and DNA, used in medicine and in molecular biology, and which may be incorporated, e.g. chemically, into an oligonucleotide or nucleic acid by formation of a phosphodiester bond or equivalent with one or two residues of the residue chain depending on whether the nucleoside analog is in a terminal or intra-chain position, respectively. Nucleic acids are chains of nucleotides, which are composed of three parts: a phosphate backbone, a pucker-shaped pentose sugar, either ribose or deoxyribose, and one of five nucleobases. A nucleoside analogue differs from a nucleoside by having any one or more of its hydroxyl, base or sugar groups altered, and the alteration does not prevent the nucleoside analogue from being incorporated into an oligonucleotide such as an aptamer, internalizing nucleic acid or tumor-homing nucleic acid.

Methods of the Present Invention

The present invention in one aspect provides a method of inhibiting tumor cell growth at a second tumor site distinct from a first tumor site in the bladder of an individual, comprising locally delivering to the bladder an effective amount of a chemotherapeutic agent (such as a nucleoside analog, for example gemcitabine), wherein the chemotherapeutic agent is delivered continuously, for example for at least about 24 hours. In some embodiments, the chemotherapeutic agent is immunogenic. In some embodiments, the chemotherapeutic agent induces a necrosis event. In some embodiment, the chemotherapeutic agent is selected from the group consisting of nucleoside analog (e.g. gemcitabine and capecitabine), taxane (e.g. docetaxel and cabazitaxel), platinum-based agent (e.g. oxaliplatin), anthracycline analogue (e.g. doxorubicin, idarubicin), and mitoxantrone. In some embodiments, the tumor cells at the second tumor site result from metastasis of a primary tumor at the first tumor site. In some embodiments, the tumor cells at the second tumor site are from a secondary tumor. In some embodiments, the tumor cells at the second tumor site are circulating tumor cells. In some embodiments, the tumor cells at the first tumor site result from metastasis of a primary tumor at the second tumor site.

In some embodiments, the chemotherapeutic agent is a nucleoside analog such as gemcitabine or capecitabine. In some embodiments, the chemotherapeutic agent is a taxane such as paclitaxel, cabazitaxel, or docetaxel. In some embodiments, the chemotherapeutic agent is a platinum-based agent such as oxaliplatin. In some embodiments, the chemotherapeutic agent is an anthracycline analogue such as doxorubicin. In some embodiments, the tumor cells at the second tumor site result from metastasis of a primary tumor at the first tumor site. For example, in some embodiments, there is provided a method of treating tumor metastasis at a site distinct from the bladder in an individual having a urothelial carcinoma of the lower tract, comprising locally delivering to the bladder an effective amount of a chemotherapeutic agent (such as a nucleoside analog, for example gemcitabine), wherein the chemotherapeutic agent is delivered continuously to the bladder, for example for at least about 24 hours. In some embodiments, there is provided a method of suppressing tumor metastasis at a site distinct from the bladder in an individual having a urothelial carcinoma of the lower tract, comprising locally delivering to the bladder an effective amount of a chemotherapeutic agent (such as a nucleoside analog, for example gemcitabine), wherein the chemotherapeutic agent is delivered continuously to the bladder, for example for at least about 24 hours. In some embodiments, the chemotherapeutic agent is delivered continuously to the bladder for about 3 weeks. In some embodiments, the chemotherapeutic agent is delivered continuously to the bladder for about 12 weeks. In some embodiments, the chemotherapeutic agent is immunogenic. In some embodiments, the chemotherapeutic agent induces a necrosis event. In some embodiments, the tumor at the second tumor site is at one or more (such as two, three, four, five, six, or seven) of: liver, lung, bone, brain, lymph node, pelvic node, peritoneum, skin, prostate, breast, colon, rectum, cervix. In some embodiments, the tumor metastatic site is at two, three, four, five, six, or more sites. In some embodiments, at least about 10% (including for example at least about any of 20%, 30%, 40%, 60%, 70%, 80%, 90%, or 100%) metastasis is inhibited. In some embodiments, the tumor metastasis is at two different sites. In some embodiments, the tumor metastasis is at two sites in the same organ. In some embodiments, the tumor metastasis is at two sites in different organs. In some embodiments, the tumor metastasis is at more than two sites. In some embodiments, the tumor metastasis is at more than two different sites. In some embodiments, for example when the metastasis is to the lung, the total area of involvement is decreased. In some embodiments, the patient has a cancer stage of M0 following treatment. In some embodiments, the patient has a cancer stage of N1 or N0 following treatment.

In some embodiments, the individual has a tumor in the bladder. In some embodiments, the individual has a urothelial carcinoma of the lower tract. In some embodiments the individual has a squamous carcinoma, adenocarcinoma, sarcomatoid, or small cell carcinoma in the bladder. In some embodiments, the individual has a histologically variant subtype of a urothelial carcinoma of the lower tract, such as pappilary, micropapillary, or carcinoma in situ. In some embodiments, the individual has an infiltrating urothelial carcinoma of lower tract such as a transitional cell carcinoma (e.g. micropappliary or spindle cell), a lymphopithelial carcinoma, a schmincke tumor, or a giant cell carcinoma. In some embodiments the individual has a non-invasive urothelial neoplasia such as a transitional cell carcinoma in situ, a non-invasive pappilary transitional cell carcinoma, a papillary transitional cell neoplasm of low malignant potential, or a urothelial papilloma. In some embodiments, the individual has a squamous neoplasm, such as a squamous cell carcinoma, a verrucous carcinoma, or a squamous cell papilloma. In some embodiments, the individual has a glandular neoplasm, such as an adenocarcinoma or a villous adenoma.

In some embodiments, there is provided a method of treating tumor metastasis at a site distinct from the bladder in an individual having bladder cancer, comprising locally delivering to the bladder an effective amount of a chemotherapeutic agent (such as a nucleoside analog, for example gemcitabine), wherein the chemotherapeutic agent is delivered continuously to the bladder, for example for at least about 24 hours. In some embodiments, the chemotherapeutic agent is delivered continuously to the bladder for about 3 weeks. In some embodiments, the chemotherapeutic agent is delivered continuously to the bladder for about 12 weeks. In some embodiments, there is provided a method of suppressing tumor metastasis at a site distinct from the bladder in an individual having bladder cancer, comprising locally delivering to the bladder an effective amount of a chemotherapeutic agent (such as a nucleoside analog, for example gemcitabine), wherein the chemotherapeutic agent is delivered continuously to the bladder, for example for at least about 24 hours. In some embodiments, at least about 10% (including for example at least about any of 20%, 30%, 40%, 60%, 70%, 80%, 90%, or 100%) metastasis is inhibited. In some embodiments, the chemotherapeutic agent is immunogenic. In some embodiments, the chemotherapeutic agent induces a necrosis event. In some embodiments, the tumor metastatic site is at one or more (such as two, three, four, five, six, or seven) of: liver, lung, bone, brain, lymph node, pelvic node, peritoneum, skin, prostate, breast, colon, rectum, cervix. In some embodiments, the tumor metastatic site is at two, three, four, five, six, or more sites. In some embodiments, the individual has muscle-invasive bladder cancer. In some embodiments, the individual has carcinoma in situ (CIS). In some embodiments, the individual is unfit for or refuses cystectomy. In some embodiments, the individual has not undergone transurethral resection of bladder tumors (TURBT). In some embodiments, the individual has undergone transurethral resection of bladder tumors (TURBT). In some embodiments, the individual has undergone transurethral resection of bladder tumors (TURBT), and has residual tumor cells at the site of resection, for example sufficient residual tumor cells to trigger an immune response. In some embodiments, the individual has Ta, Tis, T1, T2, T2a, T2b, T3, T3a, T4, T4a, or T4b cancer following TURBT. In some embodiments, the chemotherapeutic agent is delivered both prior to TURBT and after TURBT. In some embodiments, the chemotherapeutic agent concentration in the plasma of the individual during the period of continuous delivery is less than about 1 μg/mL, such as less than about any of 0.5, 0.4, 0.3, 0.2, 0.1, 0.05, 0.04, 0.03, 0.02, or 0.01 μg/mL during the delivery period. In some embodiments, the concentration of the chemotherapeutic agent or active metabolite thereof in the plasma of the individual is at a subtherapeutic level during the delivery period.

In some embodiments, there is provided a method of reducing (such as eradicating) preexisting non-bladder resident tumor metastasis at a site distinct from the bladder in an individual having a urothelial carcinoma of lower tract, comprising locally delivering to the bladder an effective amount of a chemotherapeutic agent (such as a nucleoside analog, for example gemcitabine), wherein the chemotherapeutic agent is delivered continuously to the bladder, for example for at least about 24 hours. In some embodiments, the chemotherapeutic agent is delivered continuously to the bladder for about 3 weeks. In some embodiments, the chemotherapeutic agent is delivered continuously to the bladder for about 12 weeks. In some embodiments, there is provided a method of reducing (such as eradicating) preexisting non-bladder resident tumor metastasis at a site distinct from the bladder in an individual having bladder cancer, comprising locally delivering to the bladder an effective amount of a chemotherapeutic agent (such as a nucleoside analog, for example gemcitabine), wherein the chemotherapeutic agent is delivered continuously to the bladder, for example for at least about 24 hours. In some embodiments, the chemotherapeutic agent is delivered continuously to the bladder for about 3 weeks. In some embodiments, the chemotherapeutic agent is delivered continuously to the bladder for about 12 weeks. In some embodiments, the chemotherapeutic agent is immunogenic. In some embodiments, the chemotherapeutic agent induces a necrosis event. In some embodiments, at least about 10% (including for example at least about any of 20%, 30%, 40%, 60%, 70%, 80%, 90%, or 100%) metastasis is reduced. In some embodiments, the tumor metastatic site is at one or more (such as two, three, four, five, six, or seven) of: liver, lung, bone, brain, lymph node, pelvic node, peritoneum, skin, prostate, breast, colon, rectum, and cervix. In some embodiments, the tumor metastatic site is at two, three, four, five, six, or more sites. In some embodiments, the individual has muscle-invasive bladder cancer. In some embodiments, the individual has carcinoma in situ (CIS). In some embodiments, the individual has not undergone transurethral resection of bladder tumors (TURBT). In some embodiments, the individual has undergone transurethral resection of bladder tumors (TURBT). In some embodiments, the individual has undergone transurethral resection of bladder tumors (TURBT), and has residual tumor cells at the site of resection, for example sufficient residual tumor cells to trigger an immune response. In some embodiments, the individual has Ta, Tis, T1, T2, T2a, T2b, T3, T3a, T4, T4a, or T4b cancer following TURBT. In some embodiments, the chemotherapeutic agent is delivered both prior to TURBT and after TURBT. In some embodiments, the chemotherapeutic agent concentration in the plasma of the individual during the period of continuous delivery is less than about 1 μg/mL, such as less than about any of 0.5, 0.4, 0.3, 0.2, 0.1, 0.05, 0.04, 0.03, 0.02, or 0.01 μg/mL during the delivery period. In some embodiments, the concentration of the chemotherapeutic agent or active metabolite thereof in the plasma of the individual is at a subtherapeutic level during the delivery period.

In some embodiments, there is provided a method of reducing incidence or burden of preexisting non-bladder resident tumor at a site distinct from the bladder in an individual having a urothelial carcinoma of lower tract, comprising locally delivering to the bladder an effective amount of a chemotherapeutic agent (such as a nucleoside analog, for example gemcitabine), wherein the chemotherapeutic agent is delivered continuously to the bladder, for example for at least about 24 hours. In some embodiments, there is provided a method of reducing incidence or burden of preexisting non-bladder resident tumor at a site distinct from the bladder in an individual having bladder cancer, comprising locally delivering to the bladder an effective amount of a chemotherapeutic agent (such as a nucleoside analog, for example gemcitabine), wherein the chemotherapeutic agent is delivered continuously to the bladder, for example for at least about 24 hours. In some embodiments, the tumor metastatic site is at one or more (such as two, three, four, five, six, or seven) of: liver, lung, bone, brain, lymph node, pelvic node, peritoneum, skin, prostate, breast, colon, rectum, cervix. In some embodiments, the tumor metastatic site is at two, three, four, five, six, or more sites. In some embodiments, the chemotherapeutic agent is immunogenic. In some embodiments, the chemotherapeutic agent induces a necrosis event. In some embodiments, the individual has muscle-invasive bladder cancer. In some embodiments, the individual has carcinoma in situ (CIS). In some embodiments, the individual is unfit for or refuses cystectomy. In some embodiments, the individual has not undergone transurethral resection of bladder tumors (TURBT). In some embodiments, the individual has undergone transurethral resection of bladder tumors (TURBT). In some embodiments, the individual has undergone transurethral resection of bladder tumors (TURBT), and has residual tumor cells at the site of resection, for example sufficient residual tumor cells to trigger an immune response. In some embodiments, the individual has Ta, Tis, T1, T2, T2a, T2b, T3, T3a, T4, T4a, or T4b cancer following TURBT. In some embodiments, the chemotherapeutic agent is delivered both prior to TURBT and after TURBT. In some embodiments, the chemotherapeutic agent concentration in the plasma of the individual during the period of continuous delivery is less than about 1 μg/mL, such as less than about any of 0.5, 0.4, 0.3, 0.2, 0.1, 0.05, 0.04, 0.03, 0.02, or 0.01 μg/mL during the delivery period. In some embodiments, the concentration of the chemotherapeutic agent or active metabolite thereof in the plasma of the individual is at a subtherapeutic level during the delivery period.

In some embodiments, there is provided a method of inducing immune response against a tumor cell at a second tumor site distinct from a first tumor site in the bladder of an individual, comprising locally delivering to the bladder an effective amount of a chemotherapeutic agent (such as a nucleoside analog, for example gemcitabine), wherein the chemotherapeutic agent is delivered continuously, for example for at least about 24 hours. In some embodiments, the chemotherapeutic agent is delivered continuously to the bladder for about 3 weeks. In some embodiments, the chemotherapeutic agent is delivered continuously to the bladder for about 12 weeks. In some embodiments, there is provided a method of improving tumor microenvironment for cancer therapy at a second tumor site distinct from a first tumor site in the bladder of an individual, comprising locally delivering to the bladder an effective amount of a chemotherapeutic agent (such as a nucleoside analog, for example gemcitabine), wherein the chemotherapeutic agent is delivered continuously, for example for at least about 24 hours. In some embodiments, the tumor cells at the second tumor site result from metastasis of a primary tumor at the first tumor site. In some embodiments, the tumor at the second tumor site is at one or more (such as two, three, four, five, six, or seven) of: liver, lung, bone, brain, lymph node, pelvic node, peritoneum, skin, prostate, breast, colon, rectum, cervix. In some embodiments, the tumor cells at the second tumor site are from a secondary tumor. In some embodiments, the tumor cells at the second tumor site are circulating tumor cells. In some embodiments, the tumor cells at the first tumor site result from metastasis of a primary tumor at the second tumor site. In some embodiments, the chemotherapeutic agent is selected from the group consisting of a nucleoside analog (e.g. gemcitabine and capecitabine), a taxane (e.g. docetaxel and cabazitaxel), a platinum-based agent (e.g. oxaliplatin, cisplatin or carboplatin), an anthracycline analogue (e.g. doxorubicin, idarubicin), and mitoxantrone. In some embodiments, the chemotherapeutic agent is immunogenic. In some embodiments, the chemotherapeutic agent induces a necrosis event. In some embodiments, the level of a pro-inflammatory cytokine (such as TNF-α or IFN-γ) is increased. In some embodiments, the level of an anti-inflammatory cytokine (such as TGF-β) is decreased.

In some embodiments, the level or the activity of an immune cell population is altered at the second site. In some embodiments, the level or the activity of regulatory T cells is decreased. In some embodiments, the level or the activity of effector T cells is increased. In some embodiments, the level or activity of helper T cells is increased. In some embodiments, the level or the activity of memory cells is increased. In some embodiments, the level or the activity of plasmablasts is increased. One of skill in the art will be aware of various methods to measure the presence of regulatory T cells or other immune cell population in a sample, such as immunohistochemically staining for relevant markers or performing flow cytometry or FACS analysis. For example, the level or percentage of regulatory T cells may also be decreased relatively compared to conventional T cells that are CD4+CD25−.

In some embodiments, the immune response is induced by an acute inflammation event. In some embodiments, the acute inflammation event is triggered by the continuous delivery of a chemotherapeutic agent. In some embodiments, the chemotherapeutic agent is immunogenic. In some embodiments, the chemotherapeutic agent induces a necrosis event. In some embodiments, the immune response is an innate immune response. In some embodiments, the innate immune response is characterized by an increased population of activation of antigen presenting cells such as dendritic cells and/or macrophages in the bladder or in peripheral blood or at the second tumor site. In some embodiments, the innate immune response is characterized by the increased level of tumor antigen presentation by antigen presentation cells (APCs, such as dendritic cells and/or macrophages). In some embodiments, the innate immune response is characterized by the increased level of tumor antigen presentation by antigen presentation cells (APCs, such as dendritic cells and/or macrophages) at the second site. In some embodiments, the increased level of tumor antigen presentation by APCs is triggered by the continuous delivery of the chemotherapeutic agent (such as gemcitabine).

In some embodiments, the immune response is an adaptive immune response. In some embodiments, the adaptive immune response is characterized by an increased level of immune cell population. In some embodiments, the adaptive immune response is characterized by an increased level of memory B cells in peripheral blood or tissues. In some embodiments, the adaptive immune response is characterized by an increased level of memory T cells in peripheral blood or tissues. In some embodiments, the adaptive immune response is characterized by an increased level of memory B cells at the second tumor site. In some embodiments, the adaptive immune response is characterized by an increased level of memory T cells at the second tumor site. In some embodiments, the adaptive immune response is characterized by an increased activation level of memory B cells in peripheral blood or tissues. In some embodiments, the adaptive immune response is characterized by an increased activation level of memory T cells in peripheral blood or tissues. In some embodiments, the adaptive immune response is characterized by an increased activation level of memory B cells at the second tumor site. In some embodiments, the adaptive immune response is characterized by an increased activation level of memory T cells at the second tumor site. In some embodiments, the continuous delivery of the chemotherapeutic agents induces both innate and adaptive immune response.

In some embodiments, the tumor cells at the second tumor site are from a secondary tumor. In some embodiments, there is provided a method of inhibiting the growth of a secondary tumor at a second tumor site distinct from a first tumor site in the bladder of an individual, comprising locally delivering to the bladder an effective amount of a chemotherapeutic agent (such as a nucleoside analog, for example gemcitabine), wherein the chemotherapeutic agent is delivered continuously, for example for at least about 24 hours. In some embodiments, the chemotherapeutic agent is delivered continuously to the bladder for about 3 weeks. In some embodiments, the chemotherapeutic agent is delivered continuously to the bladder for about 12 weeks. In some embodiments, the chemotherapeutic agent is immunogenic. In some embodiments, the chemotherapeutic agent induces a necrosis event. In some embodiments, the individual has bladder cancer. In some embodiments, the individual has muscle-invasive bladder cancer. In some embodiments, the individual has carcinoma in situ (CIS). In some embodiments, the individual is unfit for or refuses cystectomy. In some embodiments, the individual has not undergone transurethral resection of bladder tumors (TURBT). In some embodiments, the individual has undergone transurethral resection of bladder tumors (TURBT). In some embodiments, the individual has undergone transurethral resection of bladder tumors (TURBT), and has residual tumor cells at the site of resection, for example sufficient residual tumor cells to trigger an immune response. In some embodiments, the individual has Ta, Tis, T1, T2, T2a, T2b, T3, T3a, T4, T4a, or T4b cancer following TURBT. In some embodiments, the chemotherapeutic agent is delivered both prior to TURBT and after TURBT. In some embodiments, the chemotherapeutic agent concentration in the plasma of the individual during the period of continuous delivery is less than about 1 µg/mL, such as less than about any of 0.5, 0.4, 0.3, 0.2, 0.1, 0.05, 0.04, 0.03, 0.02, or 0.01 µg/mL during the delivery period. In some embodiments, the concentration of the chemotherapeutic agent or active metabolite thereof in the plasma of the individual is at a subtherapeutic level during the delivery period.

In some embodiments, tumor volume at the second site is reduced at least about 5%, 10%, 15%, 20%, 25%, 30%, 35%, 40%, 45%, 50%, 55%, 60%, 65%, 70%, 75% 80%, 85%, 90%, 95%, or 99% upon treatment with a chemotherapeutic agent (such as gemcitabine). In some embodiments, tumor cells at a second site distinct from a first tumor site are inhibited by delaying the appearance or development of tumor cells at a second site. In some embodiments, the growth of tumor cells at a second site is reduced for at least about 5%, 10%, 15%, 20%, 25%, 30%, 35%, 40%, 45%, 50%, 55%, 60%, 65%, 70%, 75% 80%, 85%, 90%, 95%, or 99% upon treatment with a chemotherapeutic agent (such as gemcitabine). In some embodiments, tumor cells at a second site distinct from a first tumor site are delayed in their appearance or development for at least about 7, 14, 21, 28, or 35 days upon the continuous local treatment with a chemotherapeutic agent (such as gemcitabine) at the first tumor site, as compared to the tumor cells in comparable conditions without the continuous, local delivery of the chemotherapeutic agent (such as gemcitabine) in the first site in the bladder of an individual. In some embodiments, tumor cells at a second site distinct from a first tumor site are delayed in their appearance or development for at least about 1, 2, 3, 4, 5, 6, 7, 8, 9, 10, 11 or 12 months upon the continuous, local treatment with a chemotherapeutic agent (such as gemcitabine) at the first site, as compared to the tumor cells in comparable conditions without the continuous, local delivery of the chemotherapeutic agent in the first site in the bladder of an individual.

In some embodiments, the tumor cells at the second tumor site are circulating tumor cells. In some embodiments, there is provided a method of inhibiting the release of circulating tumor cells at a second tumor site distinct from a first tumor site in the bladder of an individual, comprising locally delivering to the bladder an effective amount of a chemotherapeutic agent (such as a nucleoside analog, for example gemcitabine), wherein the chemotherapeutic agent is delivered continuously, for example for at least about 24 hours. In some embodiments, the chemotherapeutic agent is delivered continuously to the bladder for about 3 weeks. In some embodiments, the chemotherapeutic agent is delivered continuously to the bladder for about 12 weeks. In some embodiments, the chemotherapeutic agent is immunogenic. In some embodiments, the chemotherapeutic agent induces a necrosis event. In some embodiments, the individual has bladder cancer. In some embodiments, the individual has muscle-invasive bladder cancer. In some embodiments, the individual has carcinoma in situ (CIS). In some embodiments, the individual is unfit for or refuses cystectomy. In some embodiments, the individual has not undergone transurethral resection of bladder tumors (TURBT). In some embodiments, the individual has undergone transurethral resection of bladder tumors (TURBT). In some embodiments, the individual has undergone transurethral resection of bladder tumors (TURBT), and has residual tumor cells at the site of resection, for example sufficient residual tumor cells to trigger an immune response. In some embodiments, the individual has Ta, Tis, T1, T2, T2a, T2b, T3, T3a, T4, T4a, or T4b cancer following TURBT. In some embodiments, the chemotherapeutic agent is delivered both prior to TURBT and after TURBT. In some embodiments, the chemotherapeutic agent concentration in the plasma of the individual during the period of continuous delivery is less than about 1 µg/mL, such as less than about any of 0.5, 0.4, 0.3, 0.2, 0.1, 0.05, 0.04, 0.03, 0.02, or 0.01 µg/mL during the delivery period. In some embodiments, the concentration of the chemotherapeutic agent or active metabolite thereof in the individual is at a subtherapeutic level during the delivery period.

In some embodiments, circulating tumor cells are reduced upon the treatment with the chemotherapeutic agent. In some embodiments, circulating tumor cells are tumor cells in the peripheral blood of an individual. In some embodiments, circulating tumor cells are tumor cells in the cerebrospinal fluid of an individual. Circulating tumor cells can be tumor cells that have not implanted in an organ. Circulating tumor cells can be readily tested with the CELL-SEARCH CTC Test or other routine procedures. In some embodiments, the circulating tumor cells are reduced by at least about 5%, 10%, 15%, 20%, 25%, 30%, 35%, 40%, 45%, 50%, 55%, 60%, 65%, 70%, 75% 80%, 85%, 90%, 95%, or 99%. In some embodiments, the appearance or development of circulating tumor cells is delayed. In some embodiments, the growth of circulating tumor cells is reduced by at least about 5%, 10%, 15%, 20%, 25%, 30%, 35%, 40%, 45%, 50%, 55%, 60%, 65%, 70%, 75% 80%, 85%, 90%, 95%, or 99%. In some embodiments, the appearance or development of circulating tumor cells is delayed for at least about 7, 14, 21, 28 or 35 days. In some embodiments, the appearance or development of circulating tumor cells is delayed for at least about 1, 2, 3, 4, 5, 6, 7, 8, 9, 10, 11 or 12 months. In some embodiments, the appearance or development of circulating tumor cells is delayed for at least 1, 2, 3, 4, 5, 6, 7, 8, 9, 10, 11 or 12 years.

In some embodiments, the tumor cells at the first tumor site result from metastasis of a primary tumor at the second tumor site. In some embodiments, the tumor cells at the first tumor site result from a secondary tumor of an individual having a primary tumor at the second tumor site. For example, in some embodiments, the individual has a primary cancer at a second tumor site that metastasized to the bladder. In some embodiments, the individual has a primary cancer at a site distinct from the bladder and a secondary cancer in the bladder. In some embodiments, the primary cancer is selected from the group consisting of prostate cancer, breast cancer, colorectal cancer, and cervical cancer.

Thus, for example, in some embodiments, there is provided a method of treating a prostate cancer at a second tumor site distinct from the bladder of an individual, wherein the cancer has metastasized to the bladder, comprising locally delivering to the bladder an effective amount of a chemotherapeutic agent (such as a nucleoside analog, for example gemcitabine), wherein the chemotherapeutic agent is delivered continuously, for example for at least about 24 hours. In some embodiments, the chemotherapeutic agent is immunogenic. In some embodiments, the chemotherapeutic agent induces a necrosis event. In some embodiments, when the individual has prostate cancer at a second tumor site that has metastasized to the bladder, the tumor volume at the second site in the prostate is reduced by at least about 5%, 10%, 15%, 25%, 30%, 35%, 40%, 45%, 55%, 60%, 65%, 70%, 75% 80%, 85%, 90%, 95%, or 99% upon treatment with a chemotherapeutic agent (such as gemcitabine). In some embodiments, the growth of tumor cells at the second site in the prostate is reduced for at least about 5%, 10%, 15%, 25%, 30%, 35%, 40%, 45%, 55%, 60%, 65%, 70%, 75% 80%, 85%, 90%, 95%, or 99% upon treatment with a chemotherapeutic agent (such as gemcitabine). In some embodiments, the chemotherapeutic agent concentration in the plasma of the individual during the period of continuous delivery is less than about 1 µg/mL, such as less than about any of 0.5, 0.4, 0.3, 0.2, 0.1, 0.05, 0.04, 0.03, 0.02, or 0.01 µg/mL during the delivery period. In some embodiments, the concentration of the chemotherapeutic agent or active metabolite thereof in the plasma of the individual is at a subtherapeutic level during the delivery period.

In some embodiments, there is provided a method of treating breast cancer at a second tumor site distinct from the bladder of an individual, wherein the cancer has metastasized to the bladder, comprising locally delivering to the bladder an effective amount of a chemotherapeutic agent (such as a nucleoside analog, for example gemcitabine), wherein the chemotherapeutic agent is delivered continuously, for example for at least about 24 hours. In some embodiments, the chemotherapeutic agent is immunogenic. In some embodiments, the chemotherapeutic agent induces a necrosis event. In some embodiments, the metastasis to the bladder is an adenocarcinoma. In some embodiments, when the individual has breast cancer at a second tumor site that has metastasized to the bladder, the tumor volume at the second site in the breast is reduced by at least about 5%, 10%, 15%, 25%, 30%, 35%, 40%, 45%, 55%, 60%, 65%, 70%, 75% 80%, 85%, 90%, 95%, or 99% upon treatment with a chemotherapeutic agent (such as gemcitabine). In some embodiments, the growth of tumor cells at the second site in the breast is reduced for at least about 5%, 10%, 15%, 25%, 30%, 35%, 40%, 45%, 55%, 60%, 65%, 70%, 75% 80%, 85%, 90%, 95%, or 99% upon treatment with a chemotherapeutic agent (such as gemcitabine). In some embodiments, the chemotherapeutic agent concentration in the plasma of the individual during the period of continuous delivery is less than about 1 µg/mL, such as less than about any of 0.5, 0.4, 0.3, 0.2, 0.1, 0.05, 0.04, 0.03, 0.02, or 0.01 µg/mL during the delivery period. In some embodiments, the concentration of the chemotherapeutic agent or active metabolite thereof in the plasma of the individual is at a subtherapeutic level during the delivery period.

In some embodiments, there is provided a method of treating colorectal cancer at a second tumor site distinct from the bladder of an individual, wherein the cancer has metastasized to the bladder, comprising locally delivering to the bladder an effective amount of a chemotherapeutic agent (such as a nucleoside analog, for example gemcitabine), wherein the chemotherapeutic agent is delivered continuously, for example for at least about 24 hours. In some embodiments, the chemotherapeutic agent is immunogenic. In some embodiments, the chemotherapeutic agent induces a necrosis event. In some embodiments, when the individual has colorectal cancer at a second tumor site that has metastasized to the bladder, the tumor volume at the second site in the colon or rectum is reduced by at least about 5%, 10%, 15%, 25%, 30%, 35%, 40%, 45%, 55%, 60%, 65%, 70%, 75% 80%, 85%, 90%, 95%, or 99% upon treatment with a chemotherapeutic agent (such as gemcitabine). In some embodiments, the growth of tumor cells at the second site in the colon or rectum is reduced for at least about 5%, 10%, 15%, 25%, 30%, 35%, 40%, 45%, 55%, 60%, 65%, 70%, 75% 80%, 85%, 90%, 95%, or 99% upon treatment with a chemotherapeutic agent (such as gemcitabine). In some embodiments, the chemotherapeutic agent concentration in the plasma of the individual during the period of continuous delivery is less than about 1 µg/mL, such as less than about any of 0.5, 0.4, 0.3, 0.2, 0.1, 0.05, 0.04, 0.03, 0.02, or 0.01 µg/mL during the delivery period. In some embodiments, the concentration of the chemotherapeutic agent or active metabolite thereof in the plasma of the individual is at a subtherapeutic level during the delivery period.

In some embodiments, there is provided a method of treating cervical cancer at a second tumor site distinct from the bladder of an individual, wherein the cancer has metastasized to the bladder, comprising locally delivering to the bladder an effective amount of a chemotherapeutic agent (such as a nucleoside analog, for example gemcitabine), wherein the chemotherapeutic agent is delivered continuously, for example for at least about 24 hours. In some embodiments, the chemotherapeutic agent is immunogenic. In some embodiments, the chemotherapeutic agent induces a necrosis event. In some embodiments, when the individual has cervical cancer at a second tumor site that has metastasized to the bladder, the tumor volume at the second site in the cervix is reduced by at least about 5%, 10%, 15%, 25%, 30%, 35%, 40%, 45%, 55%, 60%, 65%, 70%, 75%

80%, 85%, 90%, 95%, or 99% upon treatment with a chemotherapeutic agent (such as gemcitabine). In some embodiments, the growth of tumor cells at the second site in the cervix is reduced for at least about 5%, 10%, 15%, 25%, 30%, 35%, 40%, 45%, 55%, 60%, 65%, 70%, 75% 80%, 85%, 90%, 95%, or 99% upon treatment with a chemotherapeutic agent (such as gemcitabine). In some embodiments, the chemotherapeutic agent concentration in the plasma of the individual during the period of continuous delivery is less than about 1 µg/mL, such as less than about any of 0.5, 0.4, 0.3, 0.2, 0.1, 0.05, 0.04, 0.03, 0.02, or 0.01 µg/mL during the delivery period. In some embodiments, the concentration of the chemotherapeutic agent or active metabolite thereof in the plasma of the individual is at a subtherapeutic level during the delivery period.

The chemotherapeutic agent in the methods described herein is delivered continuously to the bladder. In some embodiments, the chemotherapeutic agent is continuously delivered for at least about 24 hours, including for example at least about any of 2, 3, 4, 5, 6, or 7 days. In some embodiments the chemotherapeutic agent is continuously delivered to the bladder for 7 days or less. In some embodiments, the chemotherapeutic agent is continuously delivered to the bladder for a period of about 7 days to about three weeks. In some embodiments, the chemotherapeutic agent (such as gemcitabine) is delivered continuously to the bladder for at least about 2, 3, 4, 5, 6, 7, 8, 9, 10, 11, 12, 13 or 14 days. In some embodiments, the chemotherapeutic agent (such as gemcitabine) is delivered continuously to the bladder for at least 24-48 hours. In some embodiments, the chemotherapeutic agent (such as gemcitabine) is delivered continuously to the bladder for at least about 2-4, 4-8, 5-10, 7-14 or 18-24 days. In some embodiments, the concentration in the plasma of the individual during the period of continuous delivery is less than about 1 µg/mL, such as less than about any of 0.5, 0.4, 0.3, 0.2, 0.1, 0.05, 0.04, 0.03, 0.02, or 0.01 µg/mL during the delivery period. In some embodiments, the ratio of chemotherapeutic agent in the urine to chemotherapeutic agent in the plasma of the individual during the period of continuous delivery is greater than about 500:1 during the delivery period. Continuous delivery discussed herein also encompasses delivery of the chemotherapeutic agent in regular or irregular pulses, for example, to maintain a sustained level of the chemotherapeutic agent in the bladder. In some embodiments, the urine level of the chemotherapeutic agent in the individual is at least about 0.1 µg/mL throughout continuous delivery period. In some embodiments, the concentration of the chemotherapeutic agent or active metabolite thereof in the plasma of the individual is at a subtherapeutic level during the delivery period.

In some embodiments, the method comprises at least two separate cycles of continuous delivery. For example, the chemotherapeutic agent is continuously delivered to the bladder for a first period of time, which is followed by a rest period where no chemotherapeutic agent is delivered. Following the rest period, the chemotherapeutic agent is continuously delivered to the bladder for a second period of time. In some embodiments, the first and the second periods are each about 7 days to about three weeks. In some embodiments, the rest period is about 7 days to about two weeks. In some embodiments, the rest period is about 3, 4, 5, 6, 7, 8, 9, 10, 11, or 12 weeks. In some embodiments, the rest period is about 1-12 weeks. In some embodiments, the first and the second periods are each about 7 days to about two weeks. The methods described herein can be particularly effective when comprising at least two separate cycles of continuous delivery. Without being bound by the theory, it is believed that the first delivery period may cause presentation of neoantigen which triggers an innate and adaptive immune response. In the second dose, the neoantigen is released again which causes a stronger immune response. In some embodiments, the method comprises an induction period, a rest period, and a maintenance period, wherein the urine concentration of the chemotherapeutic agent during the induction and maintenance periods is at least about 0.1 µg/mL, and wherein the urine concentration of the chemotherapeutic agent during the rest period is less than about 0.01 µg/mL (for example below detection limit). In some embodiments, the chemotherapeutic agent concentration in the plasma of the individual during the period of continuous delivery is less than about 1 µg/mL, such as less than about any of 0.5, 0.4, 0.3, 0.2, 0.1, 0.05, 0.04, 0.03, 0.02, or 0.01 µg/mL during the delivery period. In some embodiments, the concentration of the chemotherapeutic agent or active metabolite thereof in the plasma of the individual is at a subtherapeutic level during the delivery period.

In some embodiments, the first phase is about 5-9 or 6-8 days. In some embodiments, the first phase is at least 24 or 48 hours. In some embodiments, the first phase is less than 48 hours. In some embodiments, the first phase is about 7 days. In some embodiments, the first phase is about 14 days. In some embodiments, the first phase is about 24 hours. In some embodiments, the second phase is about 5-9 or 6-8 days. In some embodiments, the second phase is at least 24 or 48 hours. In some embodiments, the second phase is less than 1.5, 3, 6, 12, 24 or 48 hours. In some embodiments, the second phase is about 7 days. In some embodiments, the second phase is about 14 days. In some embodiments, the second phase is about 24 hours. In some embodiments, the first phase is the same as the second phase. In some embodiments, the first phase is different from the second phase. In some embodiments, the rest phase is at least 24 or 48 hours. In some embodiments, the rest phase is about 7 or 14 days. In some embodiments, the rest period is less than 6, 12, 24 or 48 hours. In some embodiments, the first dose is the same as the second dose. In some embodiments, the first dose is different from the second dose. In some embodiments, each of the first dose and/or the second dose is about 1 mg/day to about 300 mg/day (such as 225 mg/day).

Other dosing regimens suitable for the methods described herein are further described in the specific section below.

Continuous delivery of chemotherapeutic agent can be carried out by various methods known in the art, including, for example, via bladder perfusion of drug solution, or via a coating substance intravesically applied to the bladder wall (for example a gel), or via an intravesical delivery device as further described below in more detail. In some embodiments, the chemotherapeutic agent is delivered by perfusion. In some embodiments, the chemotherapeutic agent is delivered by a microchip, as described for example in U.S. Publication 2008/0221557.

The delivery of the chemotherapeutic agent described herein in some embodiments can be carried out using an intravesical delivery device. Various intravesical delivery devices are described herein. In some embodiments, the intravesical device comprises a housing configured for intravesical insertion; and a dosage form comprising a chemotherapeutic agent, wherein the housing holds the dosage form and is configured to release the chemotherapeutic agent in an amount effective for the treatment of tumor metastasis or tumor at a site distinct from the bladder in an individual having a urothelial carcinoma of lower tract. In some embodiments, the intravesical drug delivery device comprises a housing which contains and controllably releases the chemotherapeutic agent and is elastically deformable between a retention shape configured to retain the device in the individual's bladder and a deployment shape for passage of the device through the individual's urethra. In some embodiments, the device comprises a drug reservoir lumen bounded by a first wall (such as a cylindrical wall) and a second wall (such as a disc shaped wall), wherein the first wall is impermeable to the drug and the second wall is permeable to the chemotherapeutic agent. In some other embodiments in which the first wall is impermeable to the chemotherapeutic agent and the second wall is permeable to the chemotherapeutic agent, the first wall and the second wall are adjacent one another and together form an annular tube defining the drug reservoir lumen. In some of these embodiments, the second wall is in the form of a strip extending at least a portion of the length of the first wall structure. In some embodiments, the device comprises at least two drug reservoir lumens, and in some embodiments each reservoir comprises a different drug contained within. In some embodiments, the chemotherapeutic agent is delivered by a device that delivers the chemotherapeutic agent in pulses. Such pulsed, staged, or intermittent dosing may be achieved by various intravesical device designs. In some embodiments, different doses of drug may be provided in separate reservoirs each configured to provide release of drug at a predefined time in vivo, for example with the use of multiple apertures each having its own associated degradable timing membrane, as described in U.S. Publication 2010/0331770 and U.S. Publication 2017/0157360, which are incorporated herein by reference.

The chemotherapeutic agent may be released from the device by osmotic pressure or by diffusion, depending on the desirable drug release profile. In some embodiments, the chemotherapeutic agent (such as gemcitabine) contained in the housing is in a non-liquid form, such as a non-liquid form is selected from the group consisting of tablets, granules, pellets, semisolids, powders, capsules, and combinations thereof. Various non-liquid forms of drug cores are further described herein.

In some embodiments, the chemotherapeutic agent is delivered from the device via passive transport. In some embodiments, passive transport is facilitated transport.

The individual described herein can be a mammal, preferably a human. In some embodiments, the individual is unsuitable for systemic chemotherapy. In some embodiments, the individual has a compromised immune system. In some embodiments, the individual is resistant to or unsuitable for chemotherapeutic therapy. In some embodiments, the individual is resistant to or unsuitable for other cancer immunotherapy. In some embodiments, the individual has a low neutrophil count. In some embodiments, the individual is ineligible for cisplatin-based combination therapy. In some embodiments, the individual has not received prior radiation therapy to the urinary bladder. In some embodiments, the individual is unwilling or unable to undergo a cystectomy. In some embodiments, the individual may undergo a cystectomy following treatment with the chemotherapeutic agent.

The effectiveness of the methods described herein can be assessed by various methods. For example, for methods of tumor treatment, the effectiveness of the method can be evaluated by tumor growth or tumor shrinkage at a second tumor site distinct from a first site in the bladder of an individual. In some embodiment, the effectiveness of the method is evaluated based on the level of one or more markers. For example, the effectiveness of the method can be determined based on the levels of TGF-beta or IL-10 of an individual. In some embodiment, the effectiveness of the method is evaluated based on the number of an immune cell population. For example, the effectiveness of the method can be determined based on the levels of regulatory T cells in a second tumor site distinct from a first site in the bladder of an individual. In some embodiments, the level of CD4+ (helper) T cells can be measured. In some embodiments, the level of CD8+ (cytotoxic) T cells can be measured. In some embodiments, the number of immune cells are measured in the spleen. In some embodiment, the effectiveness of the method is evaluated based on tumor volume in a second tumor site distinct from a first site in the bladder of an individual. In some embodiment, the effectiveness of the method is evaluated based on the number of circulating tumor cells in an individual. In some embodiments, the effectiveness of the methods can be evaluated based on the ratio of the chemotherapeutic agent and its metabolic product in the urine. For example, when the chemotherapeutic agent is gemcitabine, the effectiveness of the method may be evaluated based on the ratio of chemotherapeutic agent (e.g., gemcitabine) and its metabolite (e.g., dFdU) in the urine. For cancer treatment, a ratio below a threshold value may be indicative of effectiveness.

For example, provided herein is a method of treating a tumor at a distant at a site distinct from the bladder in an individual having a urothelial carcinoma of lower tract, comprising locally delivering to the bladder an effective amount of a chemotherapeutic agent, wherein the chemotherapeutic agent is delivered continuously to the bladder for at least about 24 hours, wherein the level of one or more cytokines indicative of an immune response is altered upon treatment. In some embodiments, the level of the cytokine during treatment is altered compared to the level prior to treatment. In some embodiments, the level of the cytokine following treatment is altered compared to the level prior to treatment. In some embodiments, the level of a cytokine is modified in an individual who has received treatment compared to an individual who has not received treatment. In some embodiments, the level of systemic TGF-β is reduced during or following treatment with a chemotherapeutic agent such as gemcitabine. In some embodiments, the level of TGF-β is reduced 2, 3, 4, 5, 6, 7, or 10 fold following treatment with the chemotherapeutic agent. In some embodiments, the level of systemic IL-10 is increased during or following treatment with a chemotherapeutic agent, such as gemcitabine. In some embodiments, the level of IL-10 is increased 1, 2, 3, 4, 5, 6, 7, or 10 fold during or following treatment with a chemotherapeutic agent such as gemcitabine. In some embodiments, the level of TNF-α is increased during or following treatment with a chemotherapeutic agent, such as gemcitabine. In some embodiments, the level of TNF-α is increased 1, 2, 3, 4, 5, 6, 7, or 10 fold during or following treatment with a chemotherapeutic agent such as gemcitabine.

In some embodiments, the methods provided herein comprise locally delivering to the bladder an effective amount of a chemotherapeutic agent, wherein the chemotherapeutic agent is delivered continuously to the bladder for at least about 24 hours, and measuring the level of one or more cytokines. In some embodiments, the level of IL-10 is measured. In some embodiments, the level of TGF-β is measured. In some embodiments, the level of TNF-α is measured. In some embodiments, the circulating level of a cytokine is measured. In some embodiments, the splenic level of a cytokine is measured. In some embodiments, the level of a cytokine in peripheral blood, serum, or plasma is measured. In some embodiments, the level of a cytokine is measured using an ELISA, flow cytometry, or radioimmunoassay.

Provided herein is a method of treating a tumor at a distant at a site distinct from the bladder in an individual having a urothelial carcinoma of lower tract, comprising locally delivering to the bladder an effective amount of a chemotherapeutic agent, wherein the chemotherapeutic agent is delivered continuously to the bladder for at least about 24 hours, wherein the level of an immune cell type is modified upon treatment. In some embodiments the level of an immune cell type is modified during treatment as compared to prior to treatment. In some embodiments, the level of an immune cell type is modified following treatment compared to prior to treatment. In some embodiments, the level of an immune cell type is modified in an individual who has been treated comparison to an individual who has not been treated. In some embodiments, the level of an immune cell type in the spleen is modified. In some embodiments, the level of an immune cell type in a peripheral blood sample is modified. In some embodiments, the level of activated helper T cells, such as CD4+/CD25+ cells, is increased during or following intravesicular treatment with a chemotherapeutic agent, such as gemcitabine. In some embodiments the level of activated cytotoxic T cells, such as CD8+/CD25+ cells, is increased during or following intravesicular treatment with a chemotherapeutic agent, such as gemcitabine. In some embodiments, the level of regulatory T cells, such as CD4+/FOXP3+ and/or CD8+FOXP3+, cells is increased during or following intravesicular treatment with a chemotherapeutic agent, such as gemcitabine.

In some embodiments, the methods provided herein comprise locally delivering to the bladder an effective amount of a chemotherapeutic agent, wherein the chemotherapeutic agent is delivered continuously to the bladder for at least about 24 hours, and measuring the level of one or more immune cell populations. In some embodiments, the number of activated helper T cells, such as CD4+/CD25+ cells is measured. In some embodiments, the number of activated cytotoxic T cells, such as CD8+/CD25+ cells, is measured. In some embodiments, the number of regulatory T cells, such as CD4+/FOXP3+ and/or CD8+FOXP3+ is measured. In some embodiments, the number of a population of immune cells is measured in the spleen. In some embodiments, the number of a population of immune cells is measured in peripheral blood. In some embodiments, the number of a population of immune cells is measured by FACS.

In some embodiments, the present invention provided herein further comprises radiation therapy. In some embodiments, the chemotherapeutic agent (such as gemcitabine) is delivered in a neoadjuvant setting. In some embodiments, the chemotherapeutic agent is delivered in an adjuvant setting. In some embodiments, the method further comprises a third therapy comprising surgery, and the delivery of the chemotherapeutic agent to the individual can be initiated at the time of the surgery, prior to the surgery, or after the surgery. In some embodiments, the delivery of the chemotherapeutic agent to the individual is initiated during a cystoscopy.

A. Patient Populations

The present invention in one aspect provides a method of inhibiting tumor cell growth at a second tumor site distinct from a first tumor site in the bladder of an individual. The methods provided herein are useful for treatment of a range of individuals having bladder cancer. In some embodiments, the individual has a urothelial carcinoma of the lower tract. In some embodiments the individual has a squamous carcinoma, sarcomatoid, or small cell carcinoma in the bladder. In some embodiments, the individual has a histologically variant subtype of a urothelial carcinoma of the lower tract, such as pappilary, micropappilary, or carcinoma in situ. In some embodiments, the individual has an infiltrating urothelial carcinoma of lower tract such as a transitional cell carcinoma (e.g. micropappliary or spindle cell), a lymphopithelial carcinoma, a schmincke tumor, or a giant cell carcinoma. In some embodiments the individual has a non-invasive urothelial neoplasia such as a transitional cell carcinoma in situ, a non-invasive pappilary transitional cell carcinoma, a papillary transitional cell neoplasm of low malignant potential, or a urothelial papilloma. In some embodiments, the individual has a squamous neoplasm, such as a squamous cell carcinoma, a verrucous carcinoma, or a squamous cell papilloma. In some embodiments, the individual has a glandular neoplasm, such as an adenocarcinoma or a villous adenoma.

In some embodiments, the individual has previously undergone chemotherapy. In some embodiments, the individual is ineligible for immunomodulatory therapy.

In some embodiments, the individual is not eligible for neoadjuvant cisplatin-based therapy comprising administering a chemotherapeutic (such as gemcitabine) locally to the bladder. In some embodiments, the individual refuses neoadjuvant cisplatin-based therapy comprising administering a chemotherapeutic agent (such as gemcitabine) locally to the bladder. In some embodiments, the individual would receive radical cystectomy but is ineligible for cisplatin-based neoadjuvant therapy.

In some embodiments, the individual is ineligible for cisplatin-based therapy based upon co-morbidities including poor performance status, poor renal function, hearing loss, peripheral neuropathy, and cardiac disease. In some embodiments, the individual is ineligible for cisplatin-based therapy based upon the absence of one or more high-risk features such as lymphovascular invasion (LVI), hydronephrosis, and concomitant carcinoma in situ (CIS).

In some embodiments, the individual is unfit or not eligible for a cystectomy. In some embodiments, the individual is ineligible for radical cystectomy under the National Comprehensive Cancer Network (NCCN) guidelines. For example, the individual is unfit for curative therapy due to frailty. Prior to the present methods, such individuals typically received palliative radiation without chemotherapy (3.5 Gy/fraction—10 treatments; or 7 Gy/fraction—7 treatments; TURBT; or no treatment). In some embodiments, the individual is unfit for platinum-based chemotherapy. In some embodiments, chemotherapy prior to radiation therapy is not recommended for the individual. In some embodiments, the individual does not receive curative therapy or systemic chemotherapy. In some embodiments, the individual has cT2-cT3 disease.

In some embodiments, the individual cannot tolerate radical cystectomy based upon the American Society of Anesthesiology (ASA) guidelines. For example, the individual who cannot tolerate radial cystectomy may be deemed medically unfit for surgery requiring general or epidural anesthesia.

In other embodiments, the individual lacks operative post-operative care infrastructure or personnel as determined by the Comprehensive Geriatric Assessment provided by the American Society of Anesthesiologists. Under these guidelines, an individual is deemed frail if he or she shows abnormal independent activities of daily living, severe malnutrition, cognitive impairment, or comorbidities cumulative illness rating scale for geriatrics (CISR-G) grades 3-4. Furthermore, under current guidelines, subjects must be deemed unfit for radical cystectomy (RC) due to comorbid conditions with a risk of mortality 5% as estimated by the American College of Surgeons risk calculator using the current procedure terminology code 51595 or 51596 for cystectomy.

In some embodiments, the bladder cancer is resected prior to administration of the chemotherapeutic agent (such as gemcitabine). In some embodiments, the individual undergoes a TURBT prior to administration of the chemotherapeutic agent (such as gemcitabine) to the bladder. In some embodiments, the tumor is maximally resected prior to administration of the gemcitabine such that no visible tumor is present. In some embodiments, the tumor is non-maximally resected prior to administration of the gemcitabine. In some embodiments, the tumor is non-maximally resected prior to administration of the gemcitabine such that residual tumor is present. In some embodiments, the patient is T0 after TURBT.

In some embodiments, the individual has undergone TURBT and has residual tumor at the site of resection, wherein the amount of residual tumor is sufficient to provide a tumor antigen to elicit an immune response. In some embodiments, about ½, ⅓, ¼, ⅕, ⅙, ⅐, ⅛, ⅑, ⅒, 1/20, 1/50, 1/100 of the original tumor amount remains after TURBT. In some embodiments at least ½, ⅓, ¼, ⅕, ⅙, ⅐, ⅛, ⅑, ⅒, 1/20, 1/50, 1/100 of the original tumor amount remains after TURBT. In some embodiments, the individual has stage Ta, Tis, T1, T2, T2a, T2b, T3, T3a, T4, T4a, or T4b cancer following TURBT. In some embodiments, a sufficient amount of residual tumor is an amount sufficient to elicit an immune response at a site distinct from the bladder. The elicitation of an immune response can be determined by the increase/decrease of a cytokine (such as IL-10, TGFβ, or INFγ) or the population of immune cells (such as regulatory T cells, activated CD4+ T helper cells, or activated CD8+ cytotoxic T cells) as described above.

The present invention also has the advantage of being useful for individuals who are not eligible for a systemic chemotherapy or hormone therapy. In some embodiments, the individual is eligible for a systemic chemotherapy or hormone therapy, but elect not to have a systemic chemotherapy or hormone therapy. In some embodiments, the individual is in the elderly, relatively frail population (such as above 70 years). In some embodiments, the individual is at least 60, 65, 70, 75, 80, 85 or 90 years old. In some embodiments, the individual is about 20 to 60 years old.

The present invention also has the advantage of being useful for individuals who have bladder cancer and are not eligible for a radiation therapy. In some embodiments, the individual is eligible for a radiation therapy, but elects not to have a radiation therapy. In some embodiments, the individual does not receive radiation therapy.

B. Dosage Regimens

The following section describes various aspects (embodiments) of dosing and treatment regimens, any and all of which apply to the methods described herein.

In some embodiments, there is provided a method of treating tumor metastasis at a site distinct from the bladder in an individual having a tumor in the bladder comprising a) a first phase of local and continuous delivery of a chemotherapeutic agent (gemcitabine) to the bladder; b) a rest period; and c) a second phase of local and continuous delivery of the same chemotherapeutic agent to the bladder. In some embodiments, the concentration of the chemotherapeutic agent or active metabolite thereof in the plasma of the individual is at a subtherapeutic level during the delivery period.

In some embodiments, there is provided a method of treating tumor metastasis at a site distinct from the bladder in an individual having a tumor in the bladder comprising administering a chemotherapeutic agent (gemcitabine) to the bladder continuously for at least 3 weeks. In some embodiments, the chemotherapeutic agent (gemcitabine) is administered locally to the bladder for about 12 weeks.

In some embodiments, the concentration of chemotherapeutic agent in the urine of the individual is less about 0.1 µg/mL during the rest period.

In some embodiments, the dosage or release rate of the chemotherapeutic agent during the different delivery periods may be the same or different. For example, in some embodiments, the chemotherapeutic agent (such as gemcitabine) is delivered continuously over at least a month, wherein the chemotherapeutic agent delivery period is at least one day, and wherein the interval between the chemotherapeutic agent (such as gemcitabine) delivery period is no more than about a week. In some embodiments, the method comprises: a) a first chemotherapeutic agent (such as gemcitabine) delivery period (such as 7 days), wherein the concentration of chemotherapeutic agent in the urine of the individual is at least about 0.1 µg/mL; b) a rest period (such as 14 days); and c) a second delivery of the same chemotherapeutic agent (such as gemcitabine) for a time period (such as 7 days), wherein the concentration of chemotherapeutic agent in the urine of the individual is greater than about 0.1 µg/mL. In some of these embodiments, the first chemotherapeutic agent delivery period is seven days, the rest period is fourteen days, and the second chemotherapeutic agent delivery period is seven days. In some embodiments, the chemotherapeutic agent is delivered on days 1-7 and days 21-28 of a treatment regimen. In some embodiments, the chemotherapeutic agent is delivered on days 1-14 and 22-34. In some embodiments, the chemotherapeutic agent is delivered on days 1-6, 1-5, or 1-4 and days 21-27, 21-26 or 21-25. In some embodiments, the chemotherapeutic agent is delivered on days 1-14 and 28-41. In some embodiments, the concentration of the chemotherapeutic agent or active metabolite thereof in the plasma of the individual is at a subtherapeutic level during the delivery period.

In some of embodiments, the first and second delivery periods are both three weeks. In some embodiments, the first and second delivery periods are both 14-21 days. In some embodiments, the first and second delivery periods are both 14 days. In some embodiments, the chemotherapeutic agent is delivered multiple times over a period of six weeks. In some embodiments, the chemotherapeutic agent is delivered multiple times over a period of 12 weeks. In some embodiments, the chemotherapeutic agent is delivered for four times for about each 14 days over a period of 12 weeks.

The chemotherapeutic agent in some embodiments is continuously delivered into the bladder for a specific time period. For example, in some embodiments, the chemotherapeutic agent is continuously delivered to the bladder for at least about 24 hours (such as at least about 2, 3, 4, 5, 6, 7, 8, 9, 10, 15, 20, 25, or 30 days). In some embodiments, the chemotherapeutic agent is continuously delivered to the bladder for about 1, 2, 3, 4, 5, 6, or 7 days.

In some embodiments, the chemotherapeutic agent may be continuously delivered for about 24 hours or more by delivering repeated shorter doses. For example, the chemotherapeutic agent may be delivered repeatedly at intervals of about 1, 2, 5, 10, 20, or 30 minutes over the course of about 24 hours or more. In some of these embodiments, the chemotherapeutic agent can be delivered using an electronic device to pump the agent into the bladder at regular intervals. For example, an external pump operably connecting a fluid drug source and a transurethral catheter having a distal end deployed into the individual's bladder can be programmed to provide intermittent or pulsed delivery of the chemotherapeutic agent.

It may be advantageous to continuously deliver the chemotherapeutic agent locally to the bladder more than once. For example, in some embodiments, the chemotherapeutic agent is delivered locally to the bladder of an individual at least twice, at least 3 times, at least 4 times, at least 5 times, or at least 10 times. In some embodiments, chemotherapeutic agent is delivered multiple times over a period of at least 2 weeks, at least 3 weeks, at least 4 weeks, at least 5 weeks, at least 6 weeks, at least 8 weeks, or at least 12 weeks. In some embodiments, the chemotherapeutic agent is delivered multiple times over a period of at least 1 month, at least 2 months, at least 3 months, at least 4 months, at least 5 months, at least 6 months, at least 12 months, or at least 18 months. For example, in some embodiments, chemotherapeutic agent is delivered locally to the bladder of an individual twice, 3 times, 4 times, 5 times, or 10 times. In some embodiments, chemotherapeutic agent is delivered multiple times over a period of one month, one month to 18 months, 2 months to 18 months, 3 months to 18 months, one month to 6 months, or one month to two months. In some embodiments, the chemotherapeutic agent is delivered locally to the bladder 4 times. In some of these embodiments, the chemotherapeutic agent is delivered locally to the bladder of the individual 4 times, wherein each chemotherapeutic agent delivery period is 3 weeks. In some of these embodiments, the chemotherapeutic agent is delivered locally to the bladder of the individual 4 times, wherein each chemotherapeutic agent delivery period is 2 weeks.

In some embodiments, the chemotherapeutic agent is delivered locally to the bladder of the individual for about 12 weeks. In some embodiments, the first delivery period is about 12 weeks. In some embodiments, the method comprises a first delivery period of about 12 weeks followed by one or more additional delivery periods, each separated by rest periods of about 1 month, 2 months, 3 months, 4 months, 5 months, 6 months, 7 months, 8 months, 9 months, 10 months, 11 months, or 12 months). In some embodiments the chemotherapeutic agent is delivered annually, for example during a maintenance phase.

In some embodiments, the chemotherapeutic agent is continuously delivered multiple times over at least one month, wherein each chemotherapeutic agent delivery period is at least one day. In some embodiments, chemotherapeutic agent is delivered at least twice over a period of at least one month. In some embodiments, chemotherapeutic agent is delivered at least three times over a period of at least one month. In some embodiments, a chemotherapeutic agent is delivered at least four times over a period of at least two months. In some embodiments, the interval between each delivery period of chemotherapeutic agent (rest period) is no more than about 4 weeks, no more than about 3 weeks, no more than about 2 weeks, or no more than about one week. In some embodiments, a chemotherapeutic agent is delivered over a least one month, wherein each delivery period of chemotherapeutic agent is at least one day, and wherein the interval between each delivery period (rest period) is no more than about one week. In some embodiments, the interval between each delivery period (rest period) is about 3 to 50 days, 3 to 30 days, 5 to 20 days or 8 to 15 days. In some embodiments the rest period is up to about 4 months (for example 1 month, 2, months, 3 months, or 4 months).

In some embodiments, the method comprises (i) placing a chemotherapeutic agent releasing intravesical device into the bladder of the individual, wherein the device remains in the bladder for 7 days and wherein the gemcitabine is continuously delivered to the bladder. In some embodiments, provided herein is a method of treating muscle invasive bladder cancer in an individual comprising (i) placing a chemotherapeutic agent releasing intravesical device into the bladder of the individual, wherein the device remains in the bladder for 7 days and wherein the chemotherapeutic agent releasing intravesical device delivers the chemotherapeutic agent passively. In some embodiments, provided herein is a method of treating muscle invasive bladder cancer in an individual comprising (i) placing a first chemotherapeutic agent releasing intravesical device into the bladder of the individual on day 0, (ii) removing the first chemotherapeutic agent releasing intravesical device at day 7, (iii) placing a second chemotherapeutic agent releasing intravesical device in the bladder of the individual at day 21, and (iv) removing the second chemotherapeutic agent releasing intravesical device at day 28. In some of these embodiments, the chemotherapeutic agent is gemcitabine and one or both of the first and second chemotherapeutic agent releasing intravesical devices contain 225 mg of gemcitabine before placement into the bladder. In some embodiments, the concentration of the chemotherapeutic agent or active metabolite thereof in the plasma of the individual is at a subtherapeutic level during the delivery period.

In some embodiments, the method comprises (i) placing a chemotherapy releasing intravesical device into the bladder of the individual, wherein the device remains in the bladder for 21 days and wherein the gemcitabine is continuously delivered to the bladder. In some embodiments, provided herein is a method of treating muscle invasive bladder cancer in an individual comprising (i) placing a chemotherapeutic agent releasing intravesical device into the bladder of the individual, wherein the device remains in the bladder for 21 days and wherein the chemotherapeutic agent releasing intravesical device delivers the chemotherapeutic agent passively. In some embodiments, provided herein is a method of treating muscle invasive bladder cancer in an individual comprising (i) placing a first chemotherapeutic agent releasing intravesical device into the bladder of the individual on day 0, (ii) removing the first chemotherapeutic agent releasing intravesical device at day 21, (iii) placing a second chemotherapeutic agent releasing intravesical device in the bladder of the individual at day 21, and (iv) removing the second chemotherapeutic agent releasing intravesical device at day 42. In some of these embodiments, the chemotherapeutic agent is gemcitabine and one or both of the first and second chemotherapeutic agent releasing intravesical devices contain 225 mg of gemcitabine before placement into the bladder. In some embodiments, the concentration of the chemotherapeutic agent or active metabolite thereof in the plasma of the individual is at a subtherapeutic level during the delivery period.

The chemotherapeutic agent may be delivered at a single release rate, or at different release rates at different time points. For example, in some embodiments, the chemotherapeutic agent is delivered in a first phase of the delivery at a first release rate followed by a second phase of the delivery having a second release rate. In some embodiments, the first release rate is faster (such as at least 2×, 3×, 4×, 5×, or 10× faster) than the second release rate. In some embodiments, the first rate is slower (such as at least 2×, 3×, 4×, 5×, or 10× slower) than the second release rate.

In some embodiments, the method comprises a first chemotherapeutic agent delivery period which a first dose is used in an induction period and a second chemotherapeutic agent delivery period in which a second dose (i.e., booster dosage) is used in a maintenance period. In some embodiments, the first dose (prime dosage) is different from the second dose (booster dosage).

In some embodiments, the chemotherapeutic agent is delivered at a dose (i.e., release rate) of from about 1 mg/day to about 300 mg/day, such as any of about 1 mg/day to about 5 mg/day, about 5 mg/day to about 10 mg/day, about 10 mg/day to about 50 mg/day, about 50 mg/day to about 100 mg/day, about 100 mg/day to about 225 mg/day (e.g., about 140 mg, about 160 mg, about 180 mg, about 200 mg, or about 220 mg) or about 200 mg/day to about 300 mg/day. In some embodiments, about 100 mg to about 500 mg of gemcitabine is delivered to the individual. In some embodiments, about 100 mg to about 200 mg of gemcitabine is delivered to the individual. In some embodiments, about 160 mg of gemcitabine is delivered to the individual over seven days. In some embodiments, about 100 mg to about 200 mg of gemcitabine is delivered to the individual over 7 days. In some embodiments, about 200 mg to about 225 mg of gemcitabine is delivered to the individual over 21 days. In some embodiment, about 225 mg of chemotherapeutic agent is delivered to the individual over 21 days. In some embodiments, 225 mg of gemcitabine is administered to the individual over seven days. In some embodiments, 225 mg of gemcitabine is administered to the individual over 21 days.

In some embodiments, the concentration of the chemotherapeutic agent (such as gemcitabine) in the urine during the delivery period is about 0.1 µg/mL to about 200 µg/mL, such as about any of 0-0.5, 0.5-1, 1-2, 2-3, 3-4, 4-5, 5-6, 6-7, 7-8, 8-9, 9-10, 10-20, 20-30, 30-40, 40-60, 60-80, 80-100, 100-150, or 150-200 µg/mL. In some embodiments, the chemotherapeutic agent concentration in the plasma of the individual during the period of continuous delivery is less than about 1 µg/mL, such as less than about any of 0.5, 0.4, 0.3, 0.2, 0.1, 0.05, 0.04, 0.03, 0.02, or 0.01 µg/mL. In some embodiments, the concentration of the chemotherapeutic agent or active metabolite thereof in the plasma of the individual is at a subtherapeutic level during the delivery period. In some embodiments, upon delivery of chemotherapeutic agent the ratio of chemotherapeutic agent in the urine to chemotherapeutic agent in the plasma of the individual during the period of continuous delivery is greater than about 500:1. In some of these embodiments, the chemotherapeutic agent is gemcitabine. In some embodiments, the plasma concentration of dFdU is less than 0.3 µg/mL upon delivery of the chemotherapeutic agent. In some embodiments, the plasma concentration of dFdU is less than 0.2 µg/mL upon delivery of the gemcitabine. In some embodiments the plasma concentration of dFdU is less than 0.1 µg/mL upon delivery of the chemotherapeutic agent. In some embodiments, the plasma concentration of dFdU is between 0.1 and 0.3 µg/mL upon delivery of the gemcitabine.

Intravesical Devices
Device Shape

In some embodiments, the methods provided herein comprise administering a chemotherapeutic agent (such as gemcitabine) using an intravesical device. In some embodiments, the intravesical device comprises a deployment shape and a retention shape. For example, the device may be elastically deformable between a relatively straightened or uncoiled shape suited for insertion through a lumen (e.g., the urethra) into the bladder of the individual (the deployment shape) and a retention shape suited to retain the device within the bladder. For the purposes of this disclosure, terms such as "relatively expanded shape," "relatively higher-profile shape," or "retention shape" generally denote any shape suited for retaining the device in the intended implantation location, including but not limited to a pretzel shape or other coiled shape (e.g., comprising bi-oval or overlapping coils) that is suited for retaining the device in the bladder. The retention shape provides that the device resists becoming entrained in urine and excreted when the individual voids. Similarly, terms such as "relatively lower-profile shape" or "deployment shape" generally denote any shape suited for deploying the drug delivery device into the body, for example the bladder, including, but not limited to, including a linear or elongated shape that is suited for deploying the device through the working channel of catheter, cystoscope, or other deployment instrument positioned in the urethra. In embodiments, the drug delivery device may naturally assume the relatively expanded shape and may be deformed, either manually or with the aid of an external apparatus, into the relatively lower-profile shape for insertion into the body. For example, the external apparatus may be an inserter configured for transurethral insertion. Once deployed the intravesical device may spontaneously or naturally return to the initial, relatively expanded shape for retention in the body. In some embodiments, the device behaves like a spring, deforming in response to a compressive load (e.g., deforming the device into a deployment shape) but spontaneously returning to a retention shape once the load is removed.

In some embodiments, the shape changing functionality of the intravesical device described in the preceding paragraph may be provided by including a shape retention frame (i.e., a "retention frame") in the device, such as those disclosed in published applications US2012/0203203, US2013/0158675, US2015/0360012, US20150165177, US2015/0165178, US20160199544, WO2014/145638, WO2015200752, and WO2011/031855, which are incorporated herein by reference. In some embodiments, the device may include a retention frame lumen in which the retention frame, which may be an elastic wire, e.g., a superelastic alloy such as nitinol, is secured. The retention frame may be configured to return spontaneously to a retention shape, such as a "pretzel" shape or another coiled shape, such as those disclosed in the applications previously incorporated. In particular, the retention frame may retain the device in the body, such as in the bladder. The retention shape provides that the device resists becoming entrained in urine and excreted when the individual voids. For example, the retention frame may have an elastic limit and modulus that allows the device to be introduced into the body in a relatively lower-profile shape, permits the device to return to the relatively expanded shape once inside the body, and impedes the device from assuming the relatively lower-profile shape within the body in response to expected forces, such as the hydrodynamic forces associated with contraction of the detrusor muscle and urination. Thus, the device may be retained in the individual's bladder once deployed, limiting or preventing accidental expulsion.

In some other embodiments, the shape changing functionality of the intravesical device may be provided by forming the device housing at least in part of a thermally shape set elastic polymer.

The material used to form the device body (i.e., the housing), at least in part, may be elastic or flexible to permit moving the device between deployment and retention shapes. When the device is in the retention shape, the retention frame portion may tend to lie inside the drug reservoir portion, although the retention frame portion can be positioned inside, outside, above, or below the drug reservoir portion in other cases. The material used to form the device body may be water permeable so that solubilizing fluid (e.g., urine) can enter the drug reservoir portion to solubilize the non-liquid forms of the chemotherapeutic agent, immunomodulating agent, additional therapeutic agent, functional agent, or combination thereof contained in the drug reservoir once the device is deployed into the bladder. For example, silicone or another biocompatible elastomeric material may be used. In other embodiments, the device body may be formed, at least in part, of a water-impermeable material.

In some embodiments, the device body is made of an elastic, biocompatible polymeric material. The material may be non-resorbable or resorbable. Example non-resorbable materials include synthetic polymers selected from poly (ethers), poly(acrylates), poly(methacrylates), poly(vinyl pyrolidones), poly(vinyl acetates), poly(urethanes), celluloses, cellulose acetates, poly(siloxanes), poly(ethylene), poly (tetrafluoroethylene) and other fluorinated polymers, and poly(siloxanes). Example resorbable materials, specifically biodegradable or bioerodible polymers, include synthetic polymers selected from poly(amides), poly(esters), poly (ester amides), poly(anhydrides), poly(orthoesters), polyphosphazenes, pseudo poly(amino acids), poly(glycerol-sebacate), poly(lactic acids), poly(glycolic acids), poly(lactic-co-glycolic acids), poly(caprolactones), poly(caprolactone) (PC) derivatives, amino alcohol-based poly(ester amides) (PEA) and poly(octane-diol citrate) (POC), and other curable bioresorbable elastomers. PC-based polymers may require additional cross-linking agents such as lysine diisocyanate or 2,2-bis(e-caprolacton-4-yl)propane to obtain elastomeric properties. Copolymers, mixtures, and combinations of the above materials also may be employed.

In some embodiments, the device body comprises silicone, thermoplastic polyurethane, ethyl vinyl acetate (EVA), or a combination thereof. In some embodiments, the device body comprises two different thermoplastic materials, one of which is a hydrophilic thermoplastic polyurethane and is drug permeable, with the other being drug-impermeable. The drug impermeable material may be a selected from the group consisting of hydrophilic polyurethane, hydrophilic polyesters, and hydrophilic polyamides. The device body may comprise an annular tube formed by an extrusion or coextrusion process, using one or more these materials, as described in U.S. Publication 2016/0310715, which is incorporated herein by reference.

Drug Core

In embodiments in which the chemotherapeutic agent is delivered from an intravesical drug delivery device, the drug may be housed in the device in various forms, which may depend on the particular mechanism by which the device controllably releases the drug into fluid (e.g., urine) in the bladder. In some embodiments, the drug is provided in a solid, semi-solid, or other non-liquid form, which advantageously may facilitate stable storage of the drug before the device is used and advantageously may enable the drug payload of the device to be stored in smaller volume than would be possible if the drug were housed in the form of a liquid solution. In some embodiments, the non-liquid form is selected from tablets, granules, pellets, powders, semisolids (e.g., an ointment, cream, paste, or gel), capsules, and combinations thereof. In one embodiment, the drug is in the form of a plurality of tablets, such as mini-tablets described in U.S. Pat. No. 8,343,516.

For example, the chemotherapeutic agent, may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

In one embodiment, the chemotherapeutic agent (such as gemcitabine) is formulated with one or more excipients that include a viscosity enhancing agent to control release of solubilized chemotherapeutic agent (such as gemcitabine) from a release aperture in the device housing. In another embodiment, the device reservoir includes both the chemotherapeutic agent and a viscosity enhancing agent, but they are not co-formulated and instead are provide in discrete regions within the reservoir, e.g., as separate tablets. Suitable viscosity enhancing agents, including but not limited to polyethylene oxide (PEO), are known in the pharmaceutical arts. In some variations of the embodiment, the viscosity enhancing agent may be provided, e.g., formulated, with urea or another osmotic agent.

In one embodiment, the chemotherapeutic agent is administered to the individual with a solubility enhancing agent. In an embodiment, the solubility enhancing agent is urea. In one embodiment, the urea is provided in a tablet or other solid form and loaded with the chemotherapeutic agent in the drug reservoir of an intravesical drug delivery device. The urea may also function, depending on the device, as an osmotic agent to facilitate generation of an osmotic pressure in a drug reservoir. In a particular embodiment, the chemotherapeutic agent and the osmotic agent are configured as separate tablets (or other solid forms) positioned within different regions of the drug reservoir as described in PCT WO 2015/026813 (Lee et al.) which is incorporated by reference herein.

In some embodiments, the device may comprise a drug reservoir lumen. In some of these embodiments, each drug reservoir lumen may hold one or several drug tablets or other solid drug units. In one embodiment, the device holds from about 10 to 100 cylindrical drug tablets, such as mini-tablets, among a number of discrete drug reservoir lumens. In certain embodiments, the mini-tablets may each have a diameter of about 1.0 to about 3.3 mm, such as about 1.5 to about 3.1 mm, and a length of about 1.5 to about 4.7 mm, such as about 2.0 to about 4.5 mm.

Drug Housing

The release of chemotherapeutic agent from the intravesical devices described herein may be driven and controlled by different mechanisms of action. In various embodiments, the drug may be released from the intravesical drug delivery device by diffusion through a wall of the drug housing, by diffusion through one or more defined apertures in a wall of the drug housing, by osmotic pressure through an aperture in the drug housing, by osmotic pressure through one or more transiently formed microchannels, by erosion of a drug formulation in contact with urine in the bladder, or by a combination thereof. In some embodiments, drug release is controlled by drug diffusion through a drug-permeable polymer or matrix component defining part of the device housing. In one embodiment, the device includes a drug-permeable polymer component.

The size of the housing, including the thickness of the wall, may be selected based on the volume of drug (and functional agent, if any) formulation(s) to be contained, the desired rate of delivery of the drug from the device body/housing, the intended site of implantation of the device within the body, the desired mechanical integrity for the device, the desired release rate or permeability to water and urine, the desired induction time before onset of initial release, and the desired method or route of insertion into the body, among other factors. In embodiments in which the housing is a tube, the tube wall thickness may be determined based on the mechanical properties and water permeability of the tube material, as a tube wall that is too thin may not have sufficient mechanical integrity while a tube wall that is too thick may experience an undesirably long induction time for initial drug release from the device and/or may not have sufficient flexibility to permit delivery through a urethra or other narrow body lumen.

In some embodiments, the housing may include an elongated, annular tube having an inner diameter from about 2 mm to about 5 mm. The drug, and functional agent if any, may be solid tablets having a diameter substantially the same as the inner diameter of the elongated annular tube. In some embodiments, the housing holds one or more first units (e.g., tablets) comprising a drug and one or more second units (e.g., tablets) comprising a functional agent which facilitates release of the drug. One or more of the first unit tablets may fill a length from about 1 cm to about 3 cm of the lumen of the tube, and one or more of the second unit tablets may fill a length from about 10 cm to about 15 cm of the lumen of the tube. In one embodiment, the ratio of volume of the first unit(s) to volume of the second unit(s) is from about 0.05 to about 0.5. Other lengths and ratios of the tablet payloads are envisioned.

In some embodiments, the housing may be an elongated, annular tube having a wall thickness from 0.1 to 0.4 mm, such as a wall thickness of 0.2 mm. The housing material may comprise one or more biocompatible elastomers. The housing material may be selected such that the housing has a durometer from 25A to 80A, such as 25A, 50A, 65A, 70A, or 80A.

In various embodiments, the intravesical device may release the drug continuously or intermittently to achieve a concentration of the drug in the bladder that produces a sustained, therapeutically effective concentration of the drug in urine in the bladder as described in the methods provided herein. In certain embodiments, the intravesical device may release the chemotherapeutic agent in an amount of from 1 mg/day to 1000 mg/day, for example from 20 mg/day to 300 mg/day or from 25 mg/day to 300 mg/day. In certain embodiments, these release rates are provided over a treatment period as described herein. In certain embodiments, these release rates are provided over a treatment period from 14 days to 21 days.

Osmotic and Diffusion Systems

Following in vivo deployment, the device releases the drug. Release may occur, as described above, due to an osmotic pressure gradient between the interior and exterior of the device, the drug passing through one or more orifices or passing pores in the device under the force of osmotic pressure. Release may also occur by diffusion, whereby the drug passes through one or more orifices or passing pores in the device and/or through a drug-permeable wall of the device, due to a drug concentration gradient between the interior and exterior of the device. Combinations of these release modes within a single device are possible, and in some embodiments are preferred in order to achieve an overall drug release profile not readily achievable from either mode individual.

In some embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. This "dissolved drug" may include micro- and nanoscale particulates of the drug in suspension that remain following substantial dissolution of the solid form of the drug and are also able to be released from the device, e.g., through an aperture in the device housing. For example, the drug may be solubilized upon contact with urine in the bladder. In certain embodiments, a water permeable wall portion of the housing is permeable to the drug in aqueous solution, such that solubilized drug is released via the wall portion, also referred to herein as "trans-wall diffusion." After the device is deployed in the individual's bladder, urine permeates through the wall, enters the reservoir, and solubilizes the chemotherapeutic agent, and the functional agent if present. In some embodiments, the drug then diffuses directly through the wall at a controlled rate, due to a drug concentration gradient between the interior and the exterior of the device. For example, the housing and/or any water or drug permeable wall portions may be silicone, a thermoplastic polyurethane, ethylene-co-vinyl acetate (EVA), or a combination thereof.

In some embodiments, the intravesical device may contain a unit concentration of 225 mg of gemcitabine. In some of these embodiments, the device may be configured to deliver about 100 to about 225 mg of gemcitabine (e.g., about 140 mg, about 160 mg, about 180 mg, about 200 mg, or about 220 mg) mg of chemotherapeutic agent to the individual over a 7 day period or over a 3 week period.

In a particular embodiment, the drug delivery device may include a permeation system as described in WO2014/145638 and U.S. Publication 2016/0310715, which are herein both incorporated by reference in its entirety. In some embodiments, the drug delivery device includes a housing having a closed drug reservoir lumen bounded by a first wall structure and a hydrophilic second wall structure; and a drug formulation comprising chemotherapeutic agent contained in the drug reservoir lumen, wherein the first wall structure is permeable or impermeable to water and impermeable to the drug, and the second wall structure is permeable to the chemotherapeutic agent.

In some embodiments, the device housing has walls bounding and defining the drug reservoir of the device that are made of a first material that serves as the first wall structure and a second material that serves as the second wall structure, such that drug release occurs essentially only through the second material. In one embodiment, the device does not include an aperture; drug release is only by diffusion through the second wall structure. As used herein, the terms "impermeable to the drug" and "impermeable to water" refer to the wall structure being substantially impermeable to the drug or to water, such that essentially no drug or water is released via the wall structure over the therapeutic release period. For use in the bladder, it is desirable that the device be compliant (i.e., easily flexed, soft feeling) during detrusor muscle contraction in order to avoid or mitigate discomfort and irritation to the patient. Thus, the durometer of the first and second materials of construction are a design consideration, and the proportion of a high durometer material may be limited in constructing a device housing of a given size while keeping it suitably compliant in the bladder. For example, Tecophilic™ thermoplastic polyurethane (Lubrizol Corp.) may have a Shore hardness greater than 70A, such as from 80A to 65D, while silicone tubing which may have a Shore hardness of from 50A to 70A. Accordingly, it can be advantageous to utilize the combination of these two different polymeric materials, rather than making the device entirely of the water-swelling hydrophilic, drug-permeable second material.

The arrangement of the first and second wall structures can take a variety of forms. In certain embodiments, the first wall structure is a cylindrical tube and the second wall structure is an end wall disposed at least one end of the cylindrical tube, or the first wall structure and the second wall structure are adjacent one another and together form a cylindrical tube. That is, drug release is controlled by drug diffusion through a drug-permeable component defining a portion of the closed device housing. The drug-permeable wall structure may be located, dimensioned, and have material properties to provide the desired rate of controlled drug diffusion from the device. In one embodiment, the drug permeable wall may include a disk stabilized in the lumen of a tube at or near an end of the tube, optionally sandwiched between an inner washer and an outer washer. In another embodiment, the drug permeable wall is part of a sidewall of a tubular housing, or part of an end plug located at the end of a tubular housing.

The length and width, e.g., wall portion formed of the water permeable material are selected to provide a desired rate of water flux into the reservoir defined by device housing. In one embodiment, the width of the water permeable wall portion may be quantified by the arc angle defining the wall when viewed in cross-section normal to the luminal axis. The water permeable region(s) of the device housing can be controlled to give a selected area of, and thus rate for, osmotic water imbibition, and yet advantageously maintain suitable overall dimensions and elasticity of the device, formed of suitable biocompatible elastomers. Advantageously by forming the device housing by a co-extrusion process, the structural variations of the water permeable region(s) can be created with conventional co-extrusion equipment by selection of the processing parameters, thereby beneficially providing the ability to cost-effectively manufacture multiple structural device configurations. In some embodiments, the length of the water permeable regions(s) runs along only a portion of the overall length of the device. In such an embodiment, larger arc angles of the water permeable region(s) can therefore be employed while keeping the rate of drug release at a desirable level over an extend period of time.

In some embodiments, the wall may have a varied thickness over the circumference of the wall, for example the drug permeable portion may have a thickness that is less than the thickness of the drug impermeable portion. Moreover, the thinner drug permeable wall structure may be disposed at various positions relative the adjacent, thicker drug impermeable wall structure. In some embodiments, drug release is controlled by drug diffusion through a drug-permeable component defining a portion of the closed device housing. The drug-permeable wall structure may be located, dimensioned, and have material properties to provide the desired rate of controlled drug diffusion from the device.

In some embodiments, the drug delivery device comprises a housing comprising a first wall structure and a second wall structure that are adjacent one another and together form a tube defining a drug reservoir lumen; and a drug contained in the drug reservoir lumen, wherein: (i) the second wall structure, or both the first wall structure and the second wall structure, are permeable to water, (ii) the first wall structure is impermeable to the drug and the second wall structure is permeable to the drug, such that the drug is releasable in vivo by diffusion through the second wall structure, (iii) the second wall structure comprises less than 90 percent of a cross sectional area of the tube, in a cross section normal to the longitudinal axis of the tube, (iv) and the first wall structure comprises a first polyurethane composition.

In some embodiments, the device comprises an elongated, elastic housing having a drug reservoir lumen extending between a first closed end and a second closed end; and a drug contained in the drug reservoir lumen, wherein (i) the housing comprises a tubular wall structure which comprises: a first annular segment formed entirely of a first material which is impermeable to the drug, and a second annular segment formed at least partially of a second material which is permeable to the drug and configured to release the drug in vivo by diffusion through the second material in the second annular segment, and (ii) the first annular segment has a first end which is integrally formed and connected with a first end of the second annular segment.

In some embodiments, the walls that define the drug reservoir lumens may have varying thickness. Housings with walls of different thicknesses may improve the housing's flexibility, compressibility, or both. Different wall thicknesses also may aid in securing a solid drug unit in the drug reservoir lumens.

In some embodiments, the intravesical device body, or housing, may include openings (e.g., at the opposed ends of an annular tube) in need of sealing following loading of the drug reservoir with the drug payload, during the assembly process. Any of these defined openings or ends of the housings, including the monolithic housing and modular housing units, may be sealed, if desired to close off an opening. This sealing may be accomplished with a sealing substance or structure. The sealing structure may be formed of biocompatible material, including a metal such as stainless steel, a polymer such as silicone, a ceramic, or sapphire, or adhesive, among others or combinations thereof. The sealing substance or structure may be biodegradable or bioerodible. In one embodiment, a medical grade silicone adhesive or other adhesive is loaded into the opening in a fluid or workable form and then cure within the housing opening to seal it. In some embodiments, the housing includes one or more predefined apertures for release of the drug from the device. These drug-release apertures are not the defined openings which are sealed. In other embodiments, the housing does not include a predefined drug-release aperture.

In some embodiments the device releases drug without a predefined drug release aperture (i.e., orifice). Release of drug from a device without a predefined drug-release aperture may be driven by diffusion or osmotic pressure. Examples of such suitable "no-orifice" release systems are described in PCT Patent Application Publication No. WO 2014/144066 (TB 130) and U.S. Patent Application Publication No. 2014/0276636 (TB 134), which are incorporated herein by reference.

In some embodiments, the drug delivery device includes an osmotic system as described in U.S. Publication 2016/0199544, U.S. Pat. No. 8,679,094, and U.S. Publication 2016/0008271, which are herein incorporated by reference.

In some embodiments, the device comprises a housing defining a reservoir; a first unit contained within the reservoir, the first unit comprising a drug; and a second unit contained within the reservoir in a position distinct from the first unit, wherein the second unit comprises a functional agent that facilitates in vivo release of the drug from housing. In some embodiments, the first unit comprises one or more solid tablets which comprise at least one drug (e.g., a chemotherapeutic agent, such as gemcitabine), and the second unit comprises one or more solid tablets (e.g., which comprise an osmotic agent, such as urea). In some embodiments, the housing is in the form of an elongated elastomeric tube having a lumen (i.e., the reservoir) in which all of the solid tablets of the first and second units are aligned and contained. The diameter of the solid tablets may be substantially the same as the diameter of the lumen.

When osmotic release is the desired drug release mode, the functional agent in the second units may include an osmotic agent that facilitates osmotic release of the drug. For example, the osmotic agent may have a higher solubility than the drug, such that the osmotic agent expedites solubilization and/or subsequent release of the drug. This beneficially allows for the delivery of low solubility or other drugs typically only delivered via diffusion, from osmotic delivery-based devices. The device may exhibit an induction period while a sufficient volume of functional agent and/or drug are solubilized to achieve the osmotic pressure gradient.

Subsequently, the device may exhibit a zero-order release rate for an extended period, followed by a reduced, non-zero-order release rate over a decay period. A desired delivery rate can be achieved by controlling/selecting various parameters of the device, including but not limited to the surface area and thickness of the water permeable wall; the permeability to water of the material used to form the wall; the shape, size, number and placement of the apertures; and the dissolution profiles of the drug and functional agent.

The devices described herein may also be configured to release drug via diffusion, alone or in combination with osmotic release. The device may be configured to allow the solubilized drug to pass through a portion of the housing or one or more apertures therein.

Alternatively, or in combination with a water permeable wall portion, the housing may include at least one aperture configured to permit a fluid to enter the reservoir in vivo. The housing may also include one or more apertures or passing pores configured to permit solubilized drug to pass there through.

In some embodiments of the osmotic system, the device housing includes a first elastomeric material that is water permeable and a second elastomeric material that is water impermeable, wherein both materials are selected to be impermeable to the drug contained in the housing.

Figure 5B:
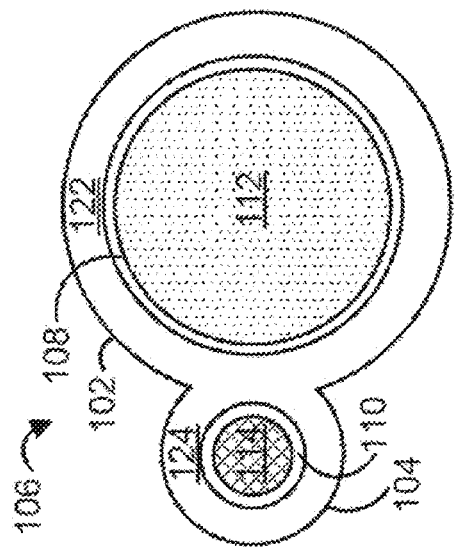
FIGS. 5A-5C show an intravesical device that can be used to provide local and continuous delivery of a chemotherapeutic agent.
Figure 5A:
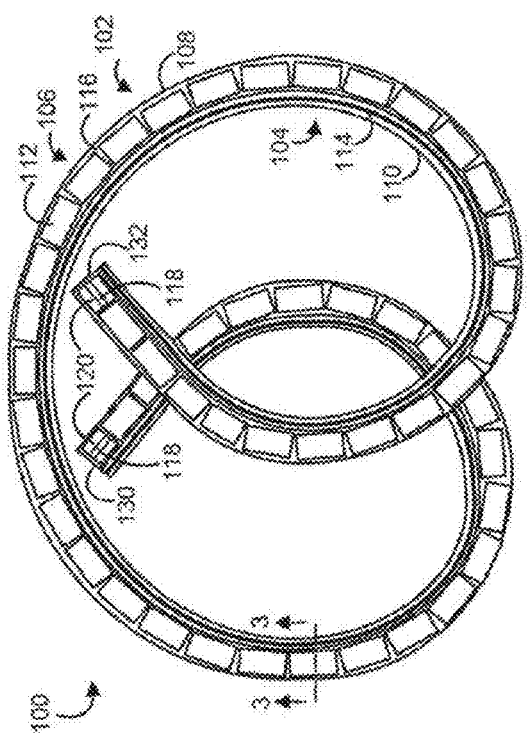
Figure 5C:
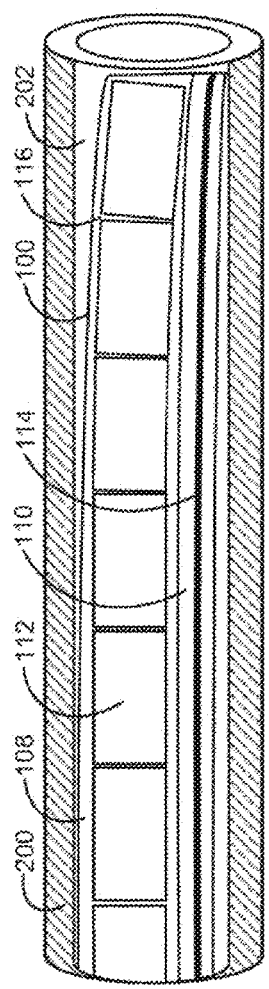

FIGS. 5A-5C illustrate one embodiment of an intravesical device useful in the methods described herein. The device 100 includes a drug reservoir portion 102 and a retention frame portion 104. In FIG. 5A, the device 100 is shown in a relatively expanded shape suited for retention within the urinary bladder of an individual. In FIG. 5C, the device 100 is shown in a relatively lower-profile shape for deployment through the working channel 202 of a deployment instrument 200, such as a cystoscope or other catheter, e.g., for insertion into and through the urethra and into the bladder of the patient. Following deployment (release of the device) into the bladder, the device 100 may assume the relatively expanded shape to retain the drug delivery device in the bladder. In the illustrated embodiment, the drug reservoir and retention frame portions 102, 104 of the drug delivery device 100 are longitudinally aligned and are integrally formed or otherwise coupled to each other along their length.

The drug delivery device 100 includes an elastic or flexible device body 106 that defines a drug reservoir lumen 108 and a retention frame lumen 110. The drug reservoir lumen 108 is configured to house a drug (e.g., a chemotherapeutic agent) which is in the form of a plurality of solid drug units 112, to form the drug reservoir portion 102. Interstices 116 or breaks formed between adjacent drug units 112 permit the drug units 112 to move with reference to each other so that the device 100 is flexible despite being loaded with drug in solid form. The retention frame lumen 110 is configured to house a retention frame 114 to form the retention frame portion 104.

As shown in the cross-sectional view of FIG. 5B, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The device body 106 may be formed integrally, such as via molding or extrusion, although separate construction and assembly of the tubes 122, 124 is possible. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. Further, the two walls 122, 124 are attached along the entire length of the device in the illustrated embodiment, although intermittent attachment can be employed.

As shown in FIG. 5A, the drug reservoir lumen 108 is loaded with a number of drug units 112 in a serial arrangement. For example, between about 10 and about 100 drug units 112 may be loaded, such as between about 20 and about 80 drug units 112. The drug units may, for example, be tablets, beads, or capsules. Essentially any number of drug units may be used, depending upon the sizes of the reservoir and the drug units. The drug reservoir lumen 108 includes open ends 130 and 132, which are shown as relatively circular openings at opposite ends of the drug reservoir lumen 108. At least one of the openings provides ingress for the drug units 112 to be placed into the drug reservoir lumen 108 during device loading and assembly.

End plugs 120 block openings 130 and 132 following loading of the drug units 112. The end plugs 120 may be cylindrical and may be secured in the drug reservoir lumen 108 by frictional engagement and/or an adhesive or other fastening means. Each end plug 120 includes an aperture 118, as illustrated, to provide a passageway for releasing drug from the drug reservoir lumen 108. In some alternative embodiments, only one of the end plugs includes an aperture. In some other alternative embodiments, neither of the end plugs includes an aperture, and in some of those embodiments, the tube wall 122 includes a defined aperture for release of drug therethrough.

The retention frame lumen 110 is loaded with the retention frame 114, which may be an elastic wire, such as a nitinol wire, (thermally) shape-set into the overlapping coiled shape shown in FIG. 5A. The retention frame 114 may have an elastic limit and modulus that allows the device 100 to be introduced into the body in a relatively lower-profile shape, permits the device 100 to return the relatively expanded shape once inside the body, and impedes the device from assuming the relatively lower-profile shape within the body in response to expected forces, such as the hydrodynamic forces associated with contraction of the detrusor muscle and urination.

Erosion-Based Systems

In some embodiments, which may be used with tablets comprising low-solubility drugs, the drug is provided in tablet form secured in the device with exposed tablet faces, such that release of drug from the device occurs by controlled erosion/dissolution, as described in U.S. Pat. No. 9,107,816. In some embodiments, the device may comprise modular housings. The modular housings are typically formed from at least two separate housing units, each unit housing at least one solid drug unit. The material from which each housing unit is formed defines at least one drug reservoir lumen capable of housing a solid drug unit. The drug reservoir lumens may have one or more defined openings. For example, the drug reservoir lumen may have two opposed openings which expose correspondingly opposed end surfaces of the at least one solid drug unit housed therein. In certain embodiments, the at least two separate housing units in the modular housings are connected, directly or indirectly, by a retention frame. In some embodiments, the modular housing units may be placed on the retention frame to form a "bracelet" design. The devices may have one housing unit or a plurality of housing units. The number of housing units may be limited only by the size of the retention frame by which they are connected.

In some embodiments, one or more of the separate housing units includes a retention frame lumen through which a shared retention frame is extended. In certain embodiments, the retention frame lumen and the drug reservoir lumen of each housing unit are arranged parallel to each other. In particular embodiments, the retention frame lumen and the drug reservoir lumen of each housing unit are arranged perpendicular to each other. In further embodiments, the retention frame lumen and the drug reservoir lumen of each housing unit are arranged at an angle other than 0° (parallel) and 90° (perpendicular), such as 5, 10, 30, 45, 60, or 85°. In further embodiments, the devices described herein include two or more housing units with at least two of the following configurations: (1) the retention frame lumen and drug reservoir lumen are arranged substantially parallel to each other, (2) the retention frame lumen and drug reservoir lumen are arranged substantially perpendicular to each other, and (3) the retention frame lumen and drug reservoir lumen are arranged at an angle other than 0° (parallel) and 90° (perpendicular).

Integrated Silicone-Drug Delivery Systems

In some embodiments, the device may comprise an elastic polymer-drug matrix as described in WO2015/200752, which is herein incorporated by reference in its entirety.

Devices with Multiple Release Portions

In some embodiments, the device includes at least two drug release portions, at least one release portion releasing drug at a different rate than another release portion as described in WO2011/031855 which is herein incorporated by reference in its entirety. The release portions may achieve different release rates by having different configurations, by housing different drug formulations, or by employing different release mechanisms, among others or combinations thereof. The release portions may be combined to achieve a desired release profile. For example, the device may include release portions that exhibit different induction or lag times before the onset of initial release, that release drug at different rates or according to different release curves after the onset of release, or that release drug for different periods before the drug load is substantially exhausted, among others or combinations thereof. The disparate release portions may be combined to achieve a desired release profile from the drug delivery device as a whole, such as a release profile that demonstrates a relatively short initial lag time and thereafter demonstrates continued release at a relatively constant rate over an extended period.

In some embodiments, the devices are loaded with drugs in the form of a number of solid drug tablets, which may be smaller in size than conventional drug tablets. Because the devices control release of the drug into the body, the drug itself may include little or no excipients that control drug release. Instead, the excipients present in the drug tablets may be present primarily or completely to facilitate the tableting process or solubilization in vivo. Thus, the devices may provide a high drug payload on a volume or weight basis, yet the devices may be small enough for in vivo deployment in a minimally invasive manner.

The drug housing also permits the egress of drug, in either liquid or semi-solid form as implanted or following in vivo solubilization. The wall may be formed from a drug-permeable material that permits drug efflux through the drug housing along its entire length. The wall also may be formed from a material that is semi-permeable to the drug depending at least in part on the drug form. For example, the wall may be permeable to the drug in one form, such as a charged form, but not another form, such as uncharged form (e.g., base form versus salt form). The wall also may include one or more openings or passageways formed completely through it that permit drug to exit the drug housing.

The drug housing may house a drug in the form of a number of solid drug tablets, which are aligned within the drug housing in a serial arrangement and are enclosed within the drug housing with sealing structures, such as plugs, that close entry openings on opposite ends of the drug housing. Interstices or breaks formed between adjacent drug tablets permit the drug tablets to move with reference to each other so that the device is flexible despite being loaded with drug in solid form.

The drug portion can have any combination of the characteristics or configurations described herein, meaning the aperture may be provided, omitted, substituted with a passing pore, or augmented with additional apertures or passing pores; the housing may have a porous wall with an open-cell structure or a closed-cell structure; one or more degradable timing structures or release modulating structures may be associated with the housing, or any combination thereof.

The drug tablets may be aligned in any arrangement other than a serial arrangement, depending on the configuration of the drug housing. The drug tablets may fill any portion of the drug housing other than the entire drug housing as illustrated. A filling material such as silicone adhesive can be used to fill any portion of the drug housing that is not loaded with drug tablets, or air may be used, increasing the buoyancy of the device. The composition of the drug tablets may be the same or may vary along the device. The drug also may be in forms other than a drug tablet, such as other liquid, semi-solid, or solid forms (e.g., granules).

In particular embodiments, the drug delivery device includes at least two discrete or segregated drug portions associated with a single retention portion. The drug portions may be separate drug housings each associated with the retention portion, or the drug portions may be separate areas within a single drug housing that is associated with the retention portion.

Each drug portion may be defined by a portion of the wall of the drug housing and at least one partition structure, which separates the drug portion from a second drug portion. The partition structure may be a plug inserted into the housing, such as a cylinder, sphere, or disk, among others, which is secured in place due to its size or with an adhesive. The partition structure also may be a portion of the housing formed directly therein, such as by molding.

A device with at least two discrete portions may be suited for controlled release of at least two drug payloads from a corresponding number of drug reservoirs. The two discrete portions may have the same configurations or different configurations as described herein. The two drug payloads may be the same as each other or may differ from each other with reference to content, such as active ingredient content or excipient content; form, such as salt form or base form; state, such as liquid, semi-solid, or solid state; among others or combinations thereof. Thus, the two discrete portions may release the two drug payloads at the same time or at different times, at the same rate or at different rates, via the same release mechanisms or different release mechanisms, or any combination thereof.

For example, one drug portion may be configured to release its drug payload relatively quickly after implantation and another drug portion may be configured to experience an induction time before beginning release, or a combination thereof. The onset of release of two payloads in different drug portions can be staged. Examples of quick release drug portions include a drug portion that operates as a relatively fast-acting osmotic pump, such as a silicone tube having a relatively thinner wall, a drug portion that is loaded with drug in a quick release form, such as liquid form or a specially formulated solid form, a drug portion associated with a relatively fast-acting degradable timing structure, or combinations thereof. Thus, the device may release drug during an initial, acute phase and during a maintenance phase.

As another example, one drug portion may be configured to release its drug payload at a relatively faster rate than the other drug payload. For example, one drug portion may house a drug payload with low water solubility for diffusive release that is initiated relatively soon after implantation, and another drug portion may house a drug payload that is highly water soluble for osmotic release after an induction period. As another example, one drug portion may house a drug payload in a liquid state for quick release through an aperture having a fast-acting degradable timing membrane, and another drug portion may house another drug payload of solid tablets for slow release following solubilization in vivo. As still another example, one drug portion may have a relatively solid wall while another drug portion may have a number of apertures or pores formed through its wall, which may increase the release rate due to diffusion, or a closed-cell porous wall, which may increase the release rate due to increased permeation of water or drug through the wall.

The release portions may be combined to achieve a desired release profile. For example, the device may include release portions that exhibit different induction or lag times before the onset of initial release, that release drug at different rates or according to different release curves after the onset of release, or that release drug for different periods before the drug load is substantially exhausted, among others or combinations thereof. The disparate release portions may be combined to achieve a desired release profile from the drug delivery device as a whole, such as a release profile that demonstrates a relatively short initial lag time and thereafter demonstrates continued release at a relatively constant rate over an extended period.

By combining multiple distinct drug portions i n a single device, the device may exhibit a desired release profile of a chemotherapeutic agent. The release profile from the device as a whole may be the sum of the release profiles of the discrete portions, for example, with the first portion exhibiting minimal lag time before the onset of release, the second portion exhibiting a short induction period as the osmotic pressure gradient develops, and the third portion exhibiting a longer delay before onset as the degradable structure dissolves or degrades. Once release begins from any one portion, the release rate may be relatively zero-order for an extended period, followed by a period of decay. It should be noted that the three discrete portions are examples, and that any number or combination of discrete portions may be used to achieve the desired release profile.

Because the different drug portions are merely segregated areas within in a single tubular housing, the device advantageously may be relatively simple to construct and deploy, and yet the different drug portions exhibit different release profiles due to the different drug payloads, aperture placement, and degradable timing structures. In other embodiments in which the drug portions use, for example, walls of different materials, thicknesses, or porous cell structures, the housing may vary along its length or separate drug housings may be used. Thus, controlled release may be achieved in a range of manners.

Gels

In another embodiment, a coating substance may be intravesically applied to the bladder wall (e.g., to an area of the urothelium inside the urinary bladder), wherein the coating substance includes the chemotherapeutic agent or other drug and one or more excipient materials that promote adherence of the coating substance to the bladder wall and provides continuous controlled release of the drug over the treatment period. The coating substance may be a mucoadhesive formulation, such as gels, ointments, creams, pastes, films, emulsion gels, tablets, polymers, or a combination thereof. Mucoadhesive formulation polymers may include hydrogels or hydrophilic polymers, polycarbophil (i.e. Carbopols, etc.), chitosan, polyvinylpyrrolidone (PVP), lectin, polyethyleneglycolated polymers, celluloses, or a combination thereof. Suitable celluloses include methyl cellulose (MC), carboxymethyl cellulose (CMC), hydroxypropyl cellulose (HPC), or combinations thereof. The coating substance may include a permeation enhancer. Non-limiting examples of permeation enhancers include dimethyl sulfoxide (DMSO), sodium carboxymethyl cellulose (NaCMC), lipids, surfactants, or combinations thereof. A coating substance may be deployed in the bladder so that the coating substance engages the bladder wall.

The coating substance may be deployed in the bladder using a deployment instrument. The deployment instrument may be any device designed to navigate natural lumens of the body to reach the intended implantation site. For deployment in the bladder, the deployment instrument is sized and shaped for passing through a urethra of a patient to a bladder. The deployment instrument may be a known device, such as a catheter or cystoscope, or a specially designed device. The deployment instrument is used to deploy the coating substance into the body and is subsequently removed from the body, leaving the coating substance wholly implanted in the body. Once so implanted, the coating substance may release drug into the body for an extended period. A comparable procedure can be used to deploy any of the devices or drugs described herein into other parts of the body through other natural lumens. For example, a deployment instrument can be used to deploy a liquid drug or drug formulation into the bladder by passing the deployment instrument through a urethra.

Exemplary Embodiments

Embodiment 1. A method of treating or suppressing tumor metastasis at a site distinct from the bladder in an individual having a urothelial carcinoma of lower tract, comprising locally delivering to the bladder an effective amount of a chemotherapeutic agent, wherein the chemotherapeutic agent is delivered continuously to the bladder for at least about 24 hours.

Embodiment 2. The method of embodiment 1, wherein the tumor metastatic site is at one or more of: liver, lung, bone, brain, lymph node, pelvic node, peritoneum, skin, prostate, breast, colon, rectum, and cervix.

Embodiment 3. The method of any one of embodiments 1-2, wherein the tumor metastasis is at two or more different sites.

Embodiment 4. A method of inhibiting tumor cell growth at a second tumor site distinct from a first tumor site in the bladder of an individual, comprising locally delivering to the bladder an effective amount of a chemotherapeutic agent, wherein the chemotherapeutic agent is delivered continuously to the bladder for at least about 24 hours.

Embodiment 5. The method of embodiment 4, wherein the tumor cells at the second tumor site are located at a pelvic node.

Embodiment 6. The method of embodiment 4, wherein the tumor cells at the second tumor site are located at a distant node.

Embodiment 7. The method of embodiment 4, wherein the tumor cells at the second tumor site are circulating tumor cells.

Embodiment 8. The method embodiment 4, wherein the tumor cells at the first tumor site result from metastasis of a primary tumor at the second tumor site.

Embodiment 9. The method of embodiment 8, wherein the tumor cells at the second site are selected from the group consisting of liver, lung, bone, brain, lymph node, pelvic node, peritoneum, skin, prostate, breast, colon, rectum, and cervix.

Embodiment 10. The method of any one of embodiments 4-9, wherein the individual has a urothelial carcinoma of lower tract.

Embodiment 11. The method of any one of embodiments 1-10, wherein the individual has bladder cancer.

Embodiment 12. The method of embodiment 11, wherein the individual has muscle invasive bladder cancer or carcinoma in situ (CIS).

Embodiment 13. The method of embodiment 11 or 12, wherein the individual is unfit for or refuses cystectomy.

Embodiment 14. The method of any one of embodiment 11-13, wherein the individual has not undergone transurethral resection of bladder tumors (TURBT).

Embodiment 15. The method of any one of embodiments 11-13, wherein the individual has undergone transurethral resection of bladder tumors (TURBT).

Embodiment 16. The method of embodiment 15, wherein the individual has residual tumor at the site of resection.

Embodiment 17. The method of any one of embodiments 1-16, wherein the chemotherapeutic agent is delivered continuously to the bladder of the individual for a period of about 7 days to about three weeks.

Embodiment 18. The method of any one of embodiments claims 1-17, wherein the method comprises an induction delivery period followed by a maintenance delivery period.

Embodiment 19. The method of embodiment 18, wherein the induction delivery period and the maintenance delivery period are separated by a rest period of about 7 to about 14 days.

Embodiment 20. The method of embodiment 18, wherein the chemotherapeutic agent is delivered at a first release rate during the induction delivery period followed and a second release rate during the maintenance delivery period.

Embodiment 21. The method of any of embodiments 1-20, wherein the chemotherapeutic agent is delivered at a dose of from about 1 mg/day to about 300 mg/day.

Embodiment 22. The method of any of embodiments 1-21, wherein the concentration of the chemotherapeutic agent in the urine is from about 0.1 µg/mL to about 200 µg/mL during the delivery period.

Embodiment 23. The method any one of embodiments 1-22, comprising
a) an induction delivery period, wherein the concentration of chemotherapeutic agent in the urine of the individual is at least about 0.1 µg/mL;
b) a rest period; and
c) a maintenance delivery period, wherein the concentration of the chemotherapeutic agent in the urine of the individual is greater than about 0.1 µg/mL.

Embodiment 24. The method of any of embodiments 1-23, wherein the individual does not receive a radiation therapy.

Embodiment 25. The method of any one of embodiments 1-24, wherein the method further comprises a radiation therapy.

Embodiment 26. The method of any one of embodiments 1-25, wherein the chemotherapeutic agent is delivered by an intravesical delivery device.

Embodiment 27. The method of embodiment 26, wherein the intravesical device contains 100 mg to 500 mg of the chemotherapeutic agent.

Embodiment 28. The method of any of embodiment 26-27, wherein the intravesical device comprises a housing configured for intravesical insertion; and a dosage form comprising chemotherapeutic agent, wherein the housing holds the dosage form and is configured to release chemotherapeutic agent.

Embodiment 29. The method of any one of embodiments 26-28, wherein the intravesical drug delivery device comprises:
a housing defining a reservoir;
a first unit contained within the reservoir, the first unit comprising an chemotherapeutic agent; and
a second unit contained within the reservoir in a position distinct from the first unit, wherein the second unit comprises a functional agent that facilitates in vivo release of the chemotherapeutic agent from the housing.

Embodiment 30. The method of any one of embodiments 26-29, wherein the intravesical drug delivery device comprises a housing which contains and controllably releases the chemotherapeutic agent and is elastically deformable between a retention shape configured to retain the device in the individual's bladder and a deployment shape for passage of the device through the individual's urethra.

Embodiment 31. The method of any one of embodiments 26-30, wherein the device comprises a drug reservoir lumen bounded by a first wall and a second wall, wherein the first wall is impermeable to the drug and the second wall is permeable to the chemotherapeutic agent.

Embodiment 32. The method of any one of embodiments 26-31 wherein the chemotherapeutic agent is released from the device by osmotic pressure.

Embodiment 33. The method of any one of embodiments 26-31, wherein the chemotherapeutic agent is released from the device by diffusion.

Embodiment 34. The method of any of embodiments 22-29, wherein the chemotherapeutic agent contained in the housing is in a non-liquid form.

Embodiment 35. The method of embodiment 34, wherein the non-liquid form is selected from the group consisting of tablets, granules, powders, semisolids, capsules, and combinations thereof.

Embodiment 36. The method of any one of embodiments 1-35, wherein the chemotherapeutic agent is selected from the group consisting of a nucleoside analog, a taxane, a platinum-based agent, and an anthracycline analogue.

Embodiment 37. The method of any one of embodiments 1-36, wherein the chemotherapeutic agent is a nucleoside analog.

Embodiment 38. The method of embodiment 37, wherein the nucleoside analog is gemcitabine.

Embodiment 39. The method of any one of embodiments 1-38, wherein the individual is human.

Embodiment 40. The method of any one of embodiments 1-39, wherein the individual is unsuitable for systemic chemotherapy.

Embodiment 41. The method of any one of embodiments 1-40, wherein the individual has a compromised immune system.

Embodiment 42. The method of any one of embodiments 1-41, wherein the individual has a high tumor burden.

EXAMPLES

Example 1

Standardized bladder perfusion system was modified to introduce bladder and subcutaneous tumors. The bladders were first surgically cannulated by placing a catheter into the bladder, fixed in place using a suture, the free end exteriorized between the scapulae.

The animals were allowed to heal. Bladder tumors were established by injecting tumor cell suspension directly into bladder wall. Subcutaneous tumor was established by injecting tumor cell suspension under skin abdominal flank.

The bladder and flank tumor model used in this study utilized immunocompetent Wistar rats, 7 to 8 weeks in age and weighing between 150 to 200 g. The bladders were first surgically cannulated by placing a P50 catheter into the bladder dome which was fixed in place using a purse string suture and the free end exteriorized between the scapulae. See FIG. 1. Upon recovery, the animals were able to freely move about in their cages and their health status was monitored daily. Per study protocol, different groups of bladder cannulated rats were next inoculated with NBTII tumor cells (Nara Bladder Tumor No. 2; ATCC® CRL1655™). This is a rat syngeneic bladder tumor cell line originally derived from tumors induced with N-butyl-N-(4-hydroxybutyl) nitrosamine. In certain treatment groups, the tumor cells were injected directly into the bladder wall as a 50 uL cell suspension of approximately $2 \times 10^6$ cells. In these treatment groups and in a control group which did not receive the bladder tumor inoculation, a tumor cell suspension of approximately 50 uL containing approximately $2.5 \times 10^6$ was also injected subcutaneously into the abdominal flank.

Figure 2:
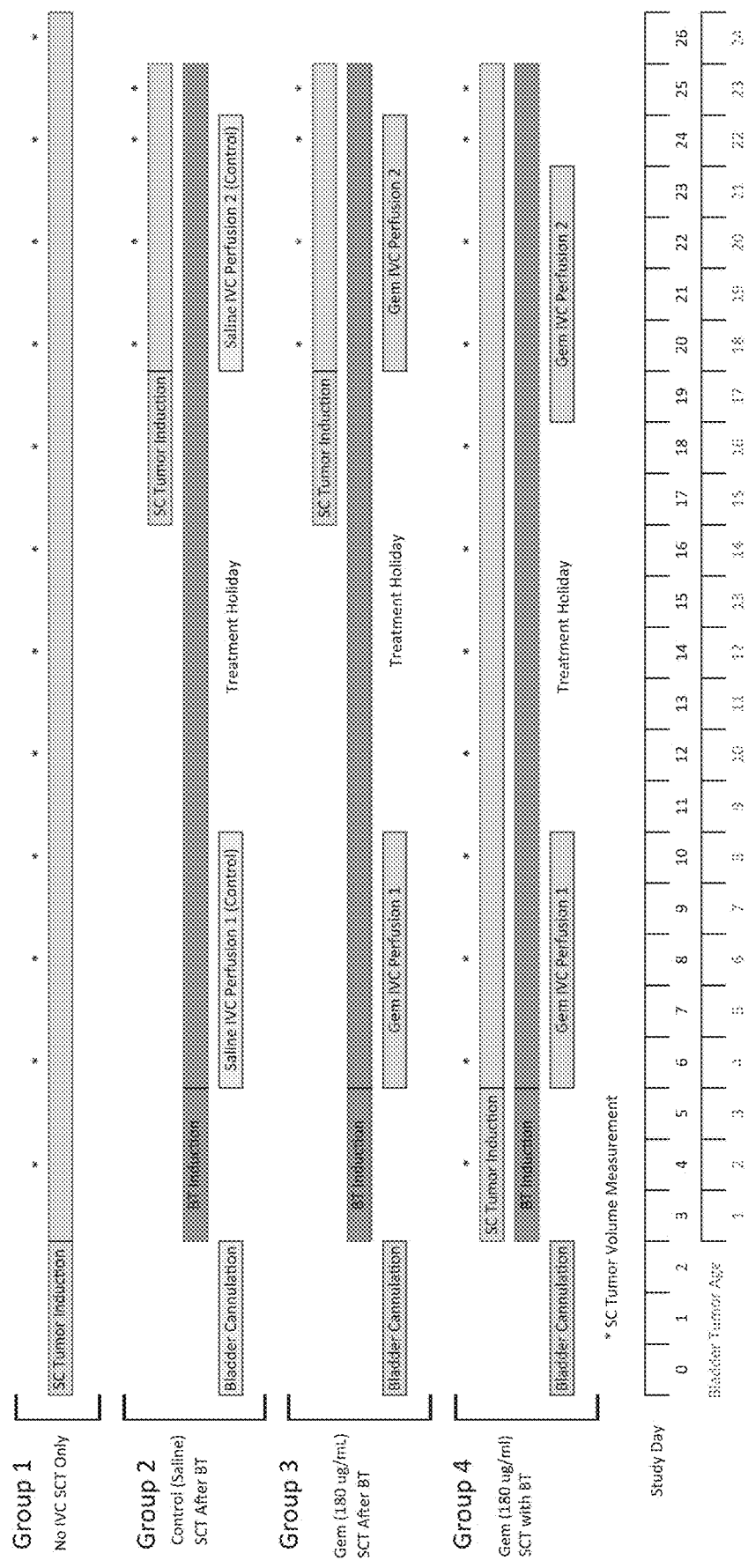
FIG. 2 shows the treatment and dosing schedule for four groups of rats: 1) untreated rats inoculated with subcutaneous tumor only; 2) untreated rats inoculated with bladder tumor and then subcutaneous tumor; 3) rats inoculated with bladder tumor, perfused with 180 µg/mL gemcitabine, and then inoculated with subcutaneous tumor and again perfused with 180 µg/mL gemcitabine; and 4) rats inoculated with bladder tumor and subcutaneous tumor simultaneously and perfused with 180 µg/mL gemcitabine twice.

The study consisted of four treatment groups as shown in FIG. 2.

Group 1 (NoIVC SCT Only, N=5) animals were inoculated with NBTII tumor cells subcutaneously only in the abdominal flank on study Day 0. No bladder cannulation procedure was performed.

Group 2 (Control, N=10) animal bladders were cannulated on study Day 0. On study Day 17, NBTII tumor cells were inoculated subcutaneously into the abdominal flank. Phosphate buffered saline was perfused via the cannula into the bladder beginning on study Day 6 at a constant rate of 0.3 mL per hour for 5 days and again beginning on Day 20 for an additional 5 day treatment period.

Group 3 (SCT after BT, N=10) animal bladders were cannulated on study Day 0 and on study Day 4 the bladders were inoculated with NBTII tumor cells. On study Day 17, the animals were also inoculated, subcutaneously, with NBTII tumor cells into the abdominal flank. Gemcitabine HCl in PBS (180 ug/mL) was perfused into the bladder via the bladder cannula beginning on study Day 6 at a constant rate of 0.3 mL per hour for 5 days and again beginning on Day 20 for an additional 5 day treatment period.

Group 4 (SCT with BT, N=10) animal bladders were cannulated on study Day 0 and on study Day 4 both the bladder and abdominal flank were inoculated with NBTII tumor cells. Gemcitabine HCl in PBS (180 ug/mL) was perfused via the cannula into the bladder beginning on study Day 6 at a constant rate of 0.3 mL per hour for 5 days and again beginning on Day 20 for an additional 5 day treatment period.

Subcutaneous tumor volumes were serially measured post inoculation every two or three days using a caliper method.

Figure 3:
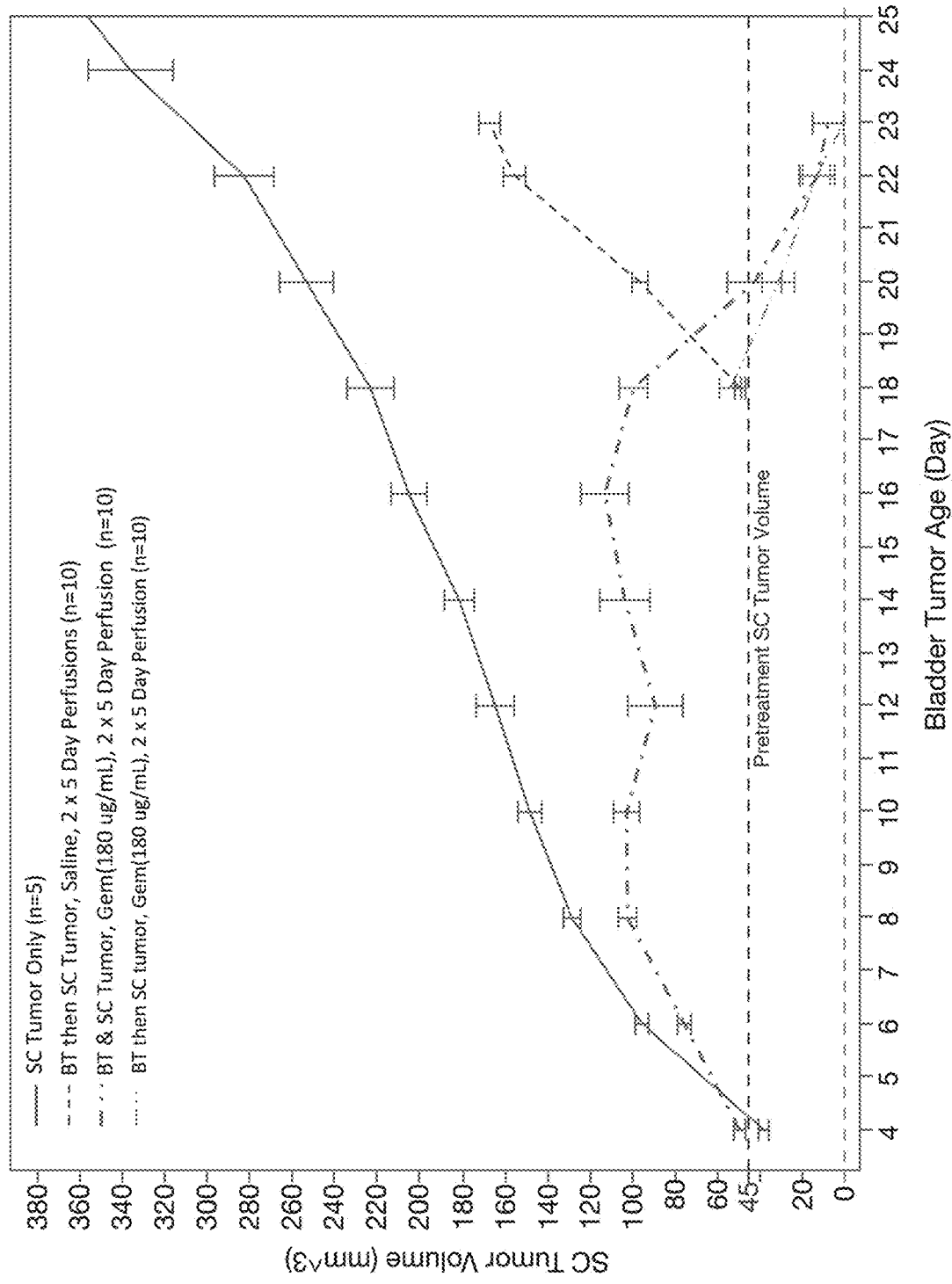
FIG. 3 shows the average volume of subcutaneous tumors in four groups of rats after introducing tumors into bladder and/or subcutaneous tissue and during the course of the treatment.
Figure 4:
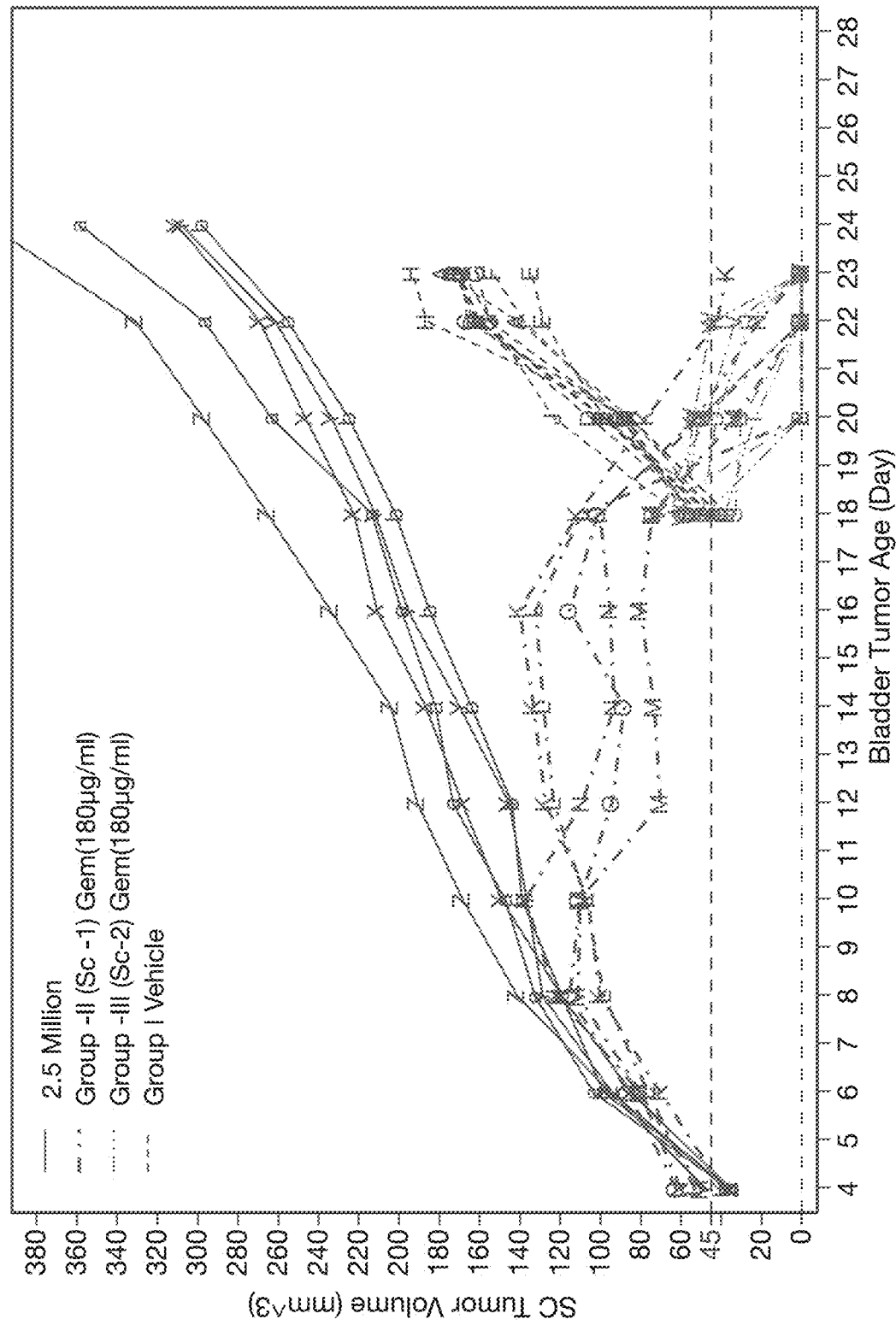
FIG. 4 shows the volume of subcutaneous tumors in each individual rat in the four groups after introducing tumors into bladder and/or subcutaneous tissue and during the course of the treatment.

The results of this study are summarized in FIGS. 3 and 4. In the Group 1 animals inoculated with only subcutaneous NBTII tumors in the abdominal flank, the tumor implantation rate was 100% which was the rate for all treatment groups. Following an initial rapid growth phase, the tumors grew at a relatively constant rate over the duration of the study. The tumor doubling rate was approximately 6 to 10 days. In comparison, subcutaneous flank tumors inoculated on study Day 17, following bladder cannulation, bladder tumor inoculation and 5 days of intravesical phosphate buffered saline perfusion were observed to grow at a very similar rate to that observed in Group 1. The similar growth rates demonstrate bladder cannulation, intravesical vehicle perfusion and the presence of a bladder tumor had no effect on the growth characteristics of the subcutaneous tumor.

In contrast, intravesical gemcitabine perfusion over two 5-day treatment cycles exhibited dramatic and unexpected effects on subcutaneous tumor growth when bladder and subcutaneous tumors were inoculated on Day 4 or when the subcutaneous tumor inoculation was delayed to study Day 17. In the Group 4 animals with both bladder and subcutaneous tumors implanted on Day 4, the subcutaneous tumors were observed to initially grow as expected. Unexpectedly, the tumor growth dramatically slowed or fully arrested in the animals by the end of the first intravesical perfusion period. Over the following 7-day drug free period, all subcutaneous tumors failed to return to their initial growth rate or show any evidence of increased growth rate. Also, unexpectedly, retreatment of the bladder tumor with a second 5-day intravesical gemcitabine treatment resulted in a rapid decline of tumor volume until all but one tumor was undetectable by palpation.

In the Group 3 animals where subcutaneous tumors were implanted on study Day 17, 14 days after bladder tumor inoculation and following the first 5-day intravesical gemcitabine perfusion period, initiation of the second gemcitabine 5 day perfusion unexpectedly resulted in a striking and immediate decline of subcutaneous tumor volume. The decline in tumor volume continued during the 5-day intravesical gemcitabine perfusion until all subcutaneous tumors were undetectable by palpation.

Standard intravesical gemcitabine treatments are typically prepared as 40 mg/mL instillations (2000 mg gemcitabine in 50 mL water). The perfusate concentrations used in this study are approximately 200-fold lower. Similarly, the total daily bladder exposure is over 1000-fold lower. Prior studies in animals and humans have shown low concentrations of intravesical gemcitabine do not produce therapeutic drug concentrations systemically. As a result, the subcutaneous tumor responses observed cannot be explained by systemic gemcitabine exposure.

The age or volume of the subcutaneous tumor at the time of intravesical treatment also did not predict the observed subcutaneous tumor responses. In Group 4, 3 day subcutaneous tumors in animals first treated with intravesical gemcitabine continued to grow for several days prior to arresting. In contrast, 3 day subcutaneous tumors in animals undergoing a second intravesical gemcitabine treatment in Group 3, immediately declined in tumor volume until the tumors were no longer detectable.

Without being bound by theory, the study results suggest an immune-mediated effect may have occurred. Gemcitabine intravesical treatment of the bladder tumor may have sensitized the animal's immune system to the bladder tumor. Upon retreatment of the bladder tumor with intravesical gemcitabine, the previously sensitized or primed immune system mounted a stronger and more effective immunological response resulting in complete eradication of all but one subcutaneous tumor in the combine Group 3 and 4 tumors.

The current results for the first time show that continuous local treatment of a bladder tumor with a chemotherapeutic can result in the shrinkage and ultimately ablation of a distant tumor. This suggests that continuous local treatment with chemotherapeutic agents such as gemcitabine can be effective for a treating a wide range of cancers including both metastases of the bladder cancer, as well as other primary tumors (e.g., breast cancer, colorectal cancer, prostate cancer, or cervical cancer) that metastasize to the bladder.

Example 2

The direct effects of low dose gemcitabine were studied in athymic rats with human derived MIBC cells, T24-TurboFP635, injected into the bladder. After 3 days tumor growth, gemcitabine or vehicle was perfused into the bladder over 5 days, yielding nominal urine concentrations of 0, 20, 40, or 80 ug/ml gemcitabine, N=6 per group. Tumor bioluminescence was measured on day 5. A companion study in immunocompetent rats inoculated with syngeneic NBTII bladder tumors, provided tumors for immunocyte analysis.

In the athymic rats with T24 tumors, significant dose dependent reductions in bladder tumor bioluminescence of 47.6%, 70.5% and 91.2% vs control were observed in the 20, 40, and 80 ug/ml groups, respectively. Flow cytometric analysis of residual tumors recovered from immunocompetent rats with NBTII tumors demonstrated a significant decrease in the proportion of tumor T regulatory cells to T effector cells of 85.2%.

Gemcitabine immunogenicity was studied in immunocompetent rats with NBTII cells injected into the bladder and subcutaneous flank tissue; flank tumors were implanted either simultaneously with bladder tumors or 14 days after bladder tumor injection. Control groups received only flank tumors, N=15, or bladder and flank tumors with vehicle perfusion, N=10. Gemcitabine treatment groups, N=10, received two 5-day bladder perfusions, yielding urine gemcitabine concentrations of 10, 20, and 40 ug/ml separated by 7 days.

Flank tumor growth was similar with tumor doubling times of 4.5 days after subcutaneous injections of 1.0, 2.5, or $5.0 \times 10^6$ cells. Flank tumor growth rates were unchanged in control rats with concomitant bladder tumors and perfused with vehicle. During the first gemcitabine perfusion cycle, flank tumor growth was fully arrested, with tumor sizes averaging only 50% of controls in rats with concomitant bladder tumors; this effect was maintained during the 7-day drug free period in the 60 ug/ml group. Initiation of the second perfusion resulted in rapid flank tumor ablation in all but one animal completing the study. A similar priming effect was observed in the 15 and 30 ug/ml groups. Delaying flank tumor implantation to 3 days before the second perfusion resulted in no tumor growth, but immediate tumor ablation.

The current results for the first time show that continuous local treatment of a bladder tumor with a chemotherapeutic can result in the shrinkage and ultimately ablation of a distant tumor. This suggests that continuous local treatment with chemotherapeutic agents such as gemcitabine can be effective for a treating a wide range of cancers including both metastases of the bladder cancer, as well as other primary tumors (e.g., breast cancer, colorectal cancer, prostate cancer, or cervical cancer) that metastasize to the bladder.

Example 3

Extending the investigation described in EXAMPLE 1, additional studies of NBTII bladder and subcutaneous tumors evaluated the effect of varying gemcitabine bladder exposures with and without simultaneous bladder tumor implantation.

In one set of experiments, gemcitabine perfusion concentrations were varied to evaluate the effect of differing bladder tumor exposures on subcutaneous tumor growth rates. Bladder cannulated rats (n=10 per treatment group) with simultaneously implanted bladder and subcutaneous NBTII tumors were studied over two treatment cycles, each separated by a 7-day drug free period, as used in the EXAMPLE 1 study.

Gemcitabine perfusion concentrations of 45 µg/ml and 90 µg/ml were tested, producing nominal urine concentrations of 10 µg/ml and 20 µg/ml respectively, representing 50% and 75% reductions vs the original study gemcitabine urine concentrations. Subcutaneous tumor growth was measured during the study as previously.

Figure 6:
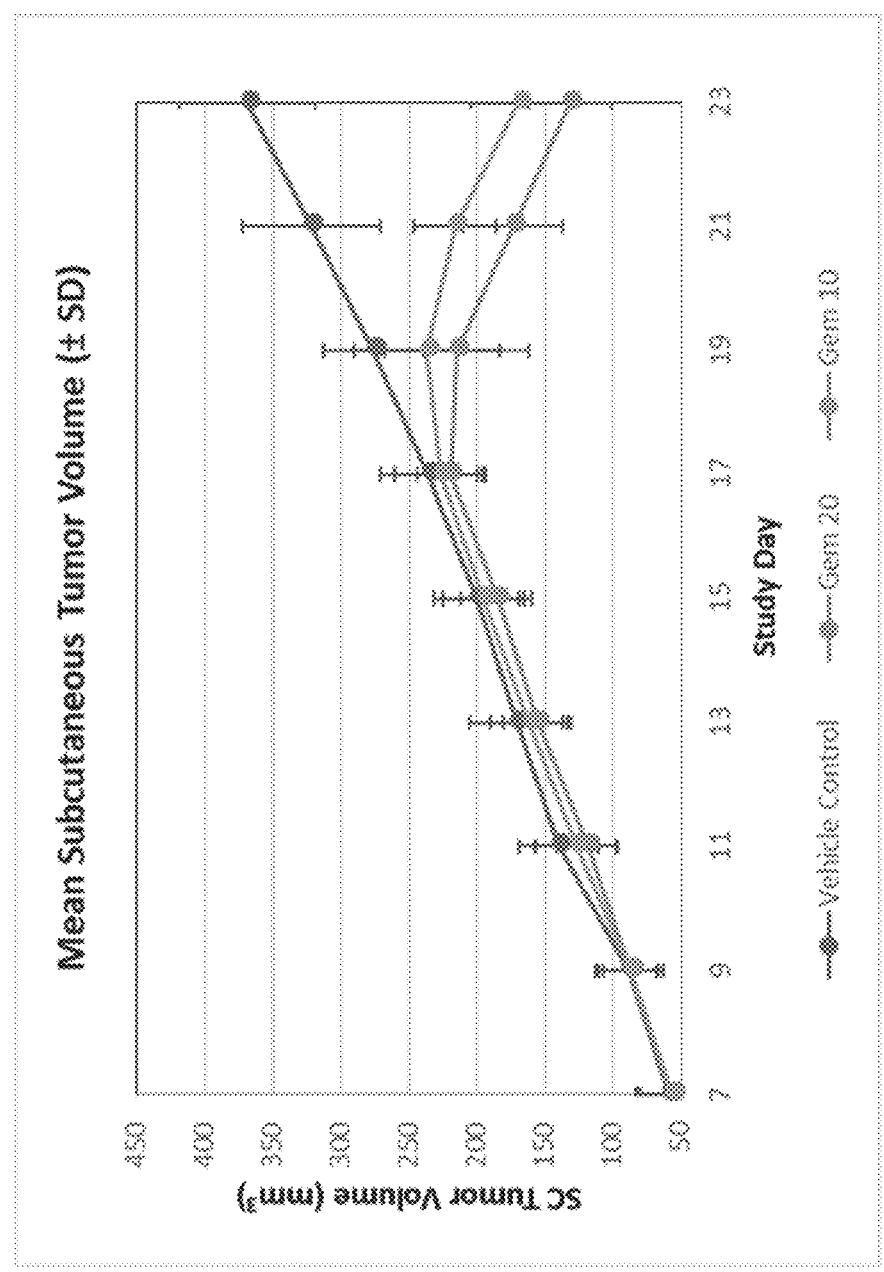
FIG. 6 shows the mean tumor volume of subcutaneous tumors in rats with bladder tumors treated with vehicle or gemcitabine perfusion concentrations of 45 µg/ml and 90 µg/ml, producing nominal urine concentrations of 10 µg/ml and 20 µg/ml.

As shown in FIG. 6, control subcutaneous tumors grew throughout the study period as in the prior example. Gemcitabine, at reduced urine concentrations, produced a dose related reduction in subcutaneous tumor volume. Similar to EXAMPLE 1 findings, subcutaneous tumor volume was significantly decreased to near ablation during the second treatment cycle.

Combined these results indicate that lower gemcitabine exposures are able to prime the immune system against subcutaneous NBTII tumors. The second gemcitabine treatment cycle continued to rapidly diminish subcutaneous tumor volumes despite the reduced gemcitabine urine concentrations tested.

Example 4

Figure 7:
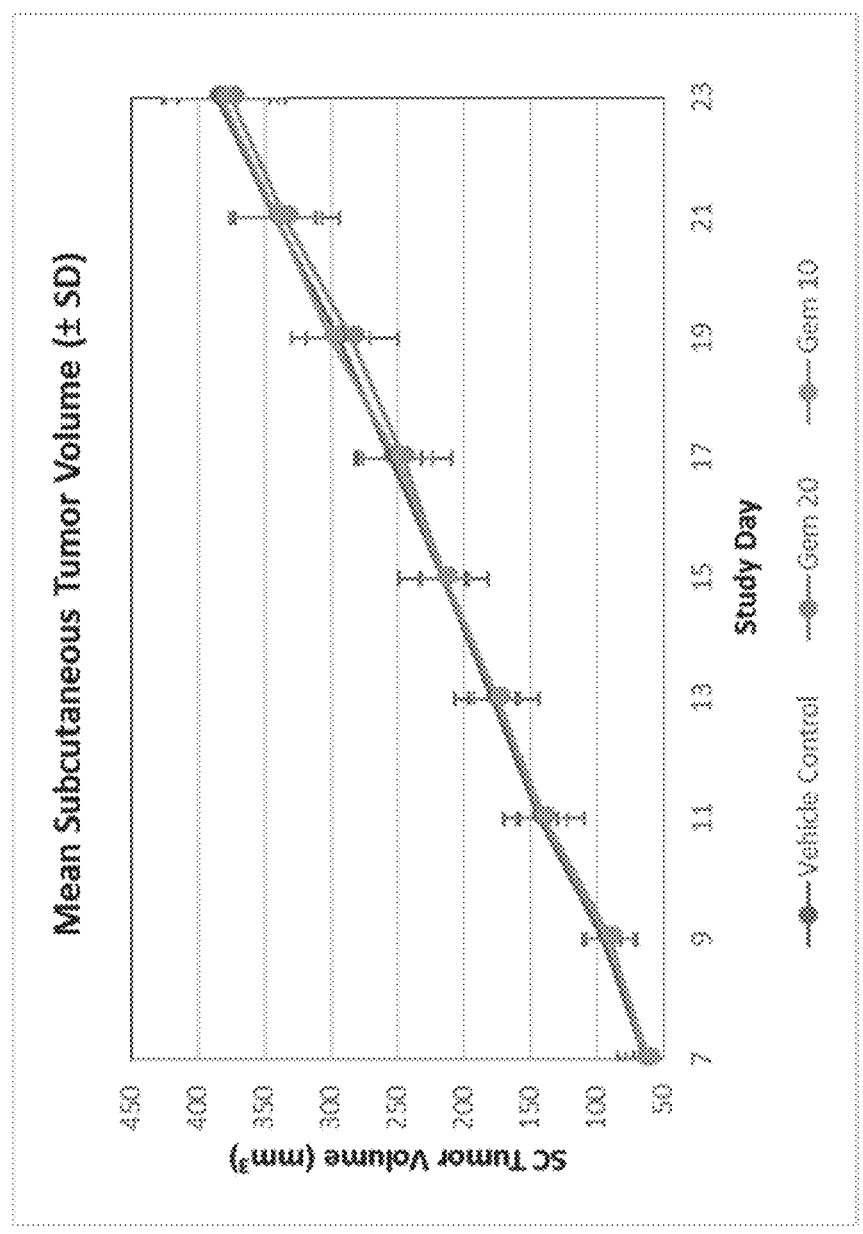
FIG. 7 shows the mean tumor volume of subcutaneous tumors in rats without bladder tumors treated with vehicle or gemcitabine perfusion concentrations of 45 µg/ml and 90 µg/ml, producing nominal urine concentrations of 10 µg/ml and 20 µg/ml.

To confirm the observed effects on subcutaneous tumor growth is the result of the local action of intravesical gemcitabine on bladder tumors, an additional series of experiments were completed in which bladder cannulated rats were implanted with only subcutaneous NBTII tumors. The animals were then treated with two perfusion cycles of intravesical gemcitabine as in the previous experiments. As shown in FIG. 7, subcutaneous tumors continued to grow throughout both treatment cycles and, in both vehicle, and gemcitabine treated bladders. These findings both confirm the presence of a bladder tumor is required and the observed reductions in subcutaneous tumors are mediated immunologically.

Example 5

Rats inoculated with NBTII tumors then administered intravesicular gemcitabine at tumoricidal doses resulted in significant alterations in circulating cytokine levels.

Intravesicular gemcitabine perfusion of 180 ug/ml solution produces an average gemcitabine urine concentration of 40 ug/mL which has been demonstrated to significantly reduce bladder tumor growth after inoculation with T24 or NBTII tumor cells.

Figure 8:
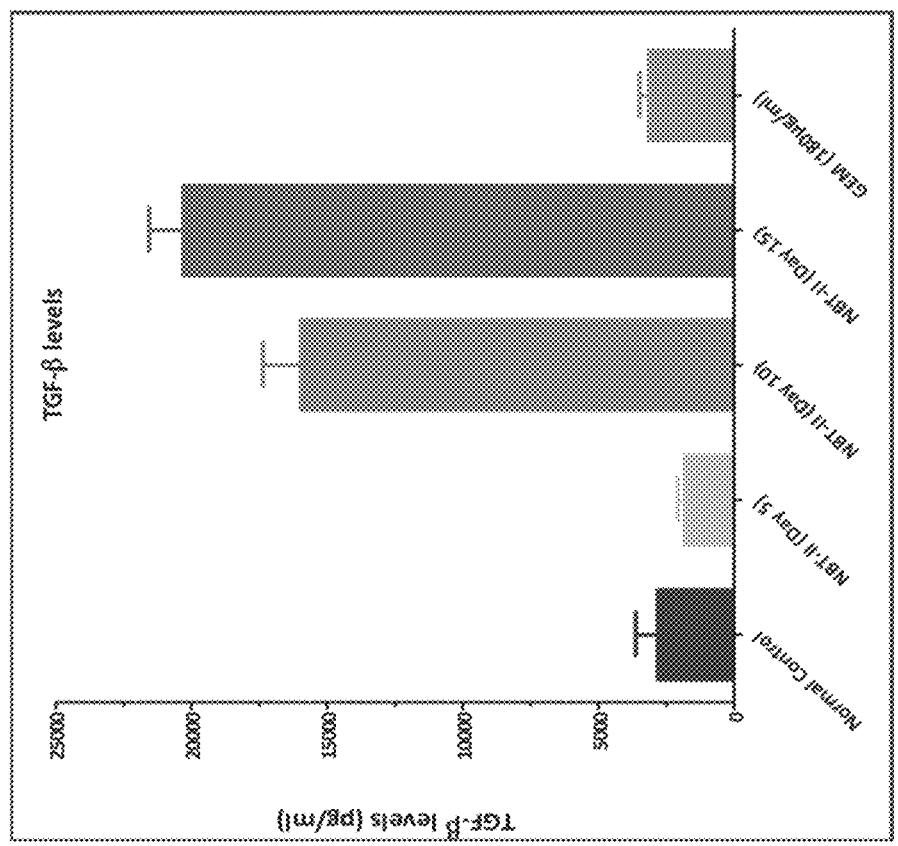
FIG. 8 shows circulating TGF-β levels in rats inoculated with NBT-II bladder tumor cells, either without gemcitabine treatment (NBT-II) or upon intravesicular treatment with gemcitabine (GEM).

As shown in FIG. 8, after bladder tumor inoculation in rats (n=8) and as tumors develop in the bladder, circulating TGF-β plasma concentrations significantly increased by day 10 and 15 compared to normal animals (n=3) without tumor inoculation. TGF-β drives Treg cell expression which in turn suppresses both local and systemic CD4 and CD8 T cell response against the bladder tumor. In contrast, low concentration intravesical gemcitabine perfusions suppressed TGF-β production and corresponding immune system inhibition.

Figure 9:
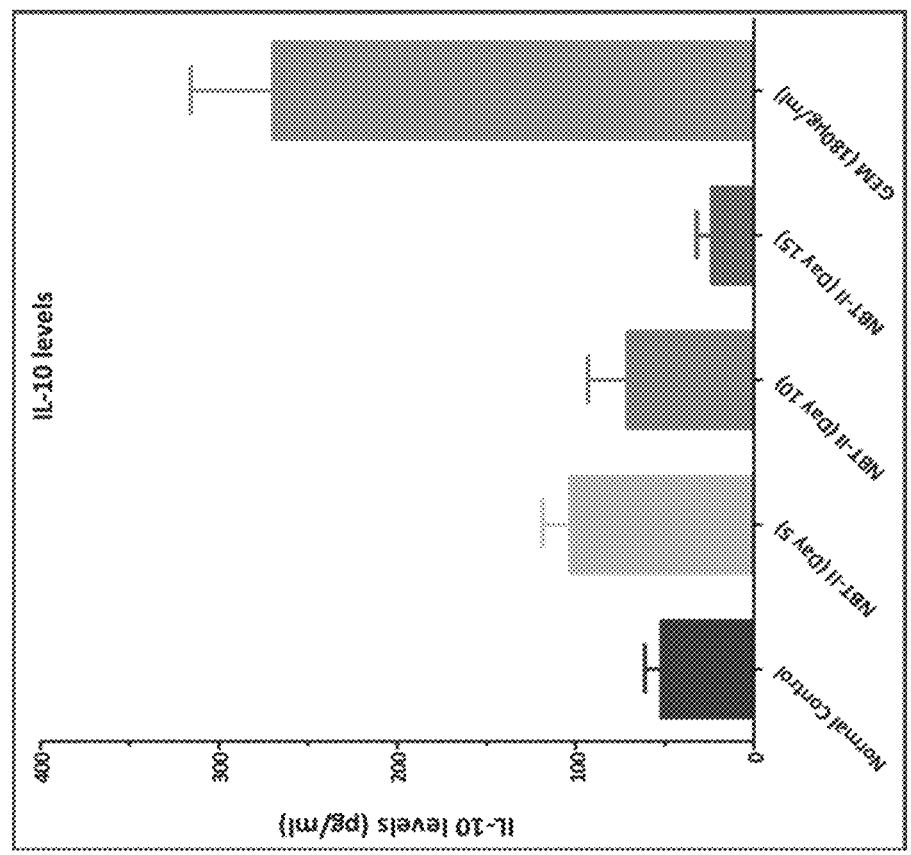
FIG. 9 shows circulating IL-10 levels in rats inoculated with NBT-II bladder tumor cells, either without gemcitabine treatment (NBT-II) or upon intravesicular treatment with gemcitabine (GEM).
Figure 10:
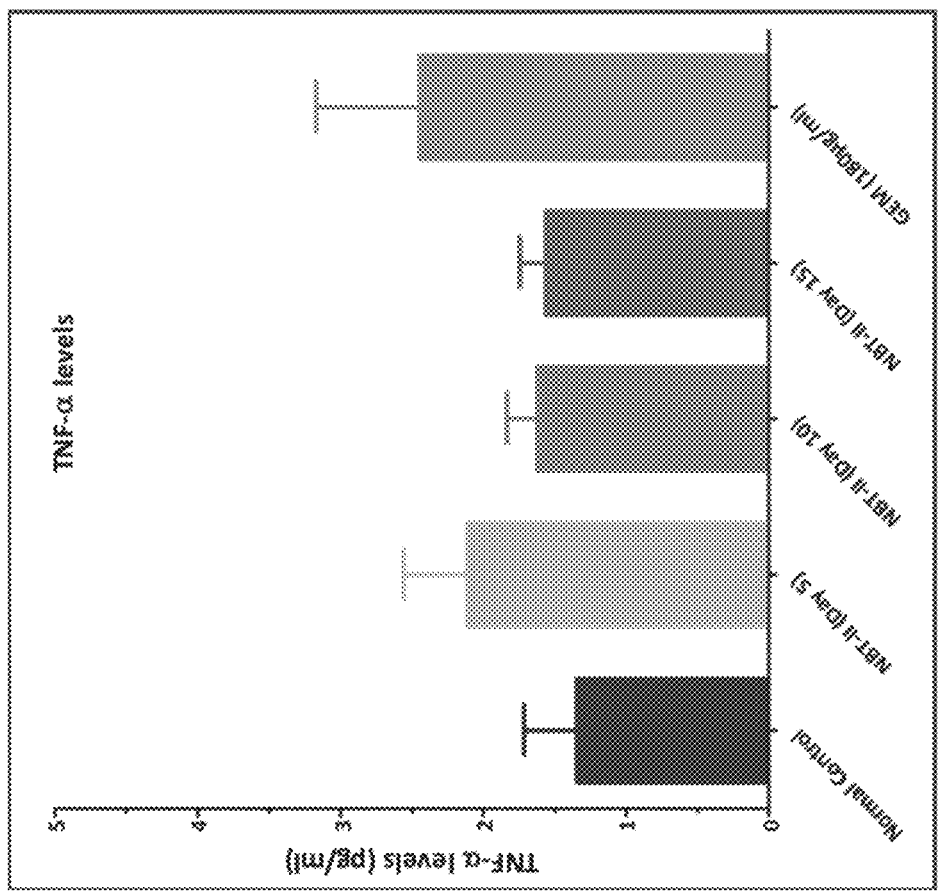
FIG. 10 shows circulating TNF-α levels in rats inoculated with NBT-II bladder tumor cells, either without gemcitabine treatment (NBT-II) or upon intravesicular treatment with gemcitabine (GEM).

Evidence of an adaptive systemic immune response was also observed in rats inoculated with bladder tumor then treated intravesical gemcitabine when flow cytometry was performed on the spleens of treated animals. Spleens of animals treated with intravesicular gemcitabine showed increased IL-10 levels, as shown in FIG. 9. IL-10 increases associated with acute treatment are known to facilitate T cell mediated antitumor effects. TNF-α was also moderately increased upon treatment with gemcitabine, as shown in FIG. 10.

Example 6

Figure 11:
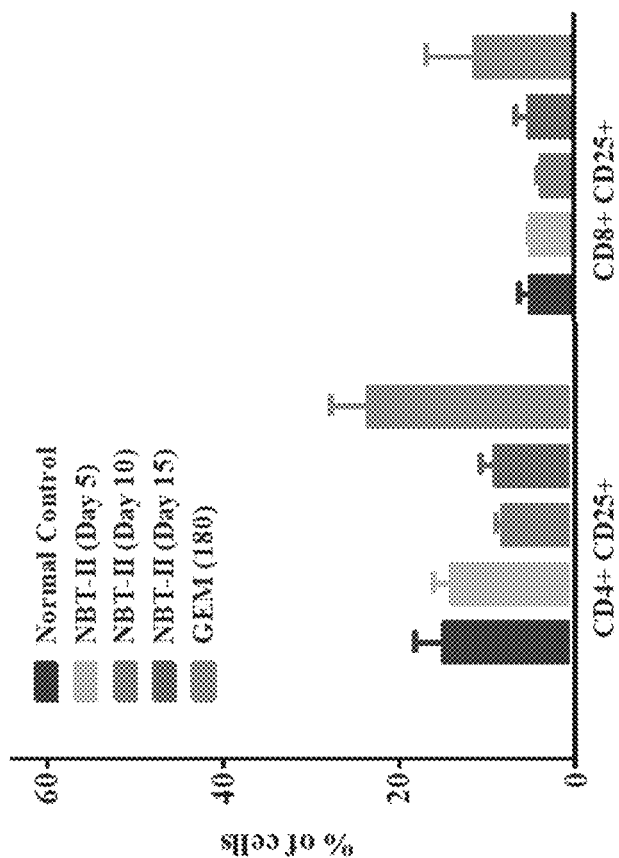
FIG. 11 shows activated CD4 and CD8 splenic T cell populations in tumor bearing rats administered intravesicular gemcitabine.

Rats were inoculated with NBT-II tumors and the number of activated CD4 and CD8 cells in the spleen was assessed by flow cytometry either in rats treated with intravesicular gemcitabine or untreated rats. As shown in FIG. 11, rats that were inoculated with NBT-II tumors and did not receive intravesicular gemcitabine showed a decrease in activated CD8 and CD4 cells. Intravesicular gemcitabine increased the percentage of activated CD4 and CD8 cells, thus indicating activation of the immune system against the tumor.

Figure 12:
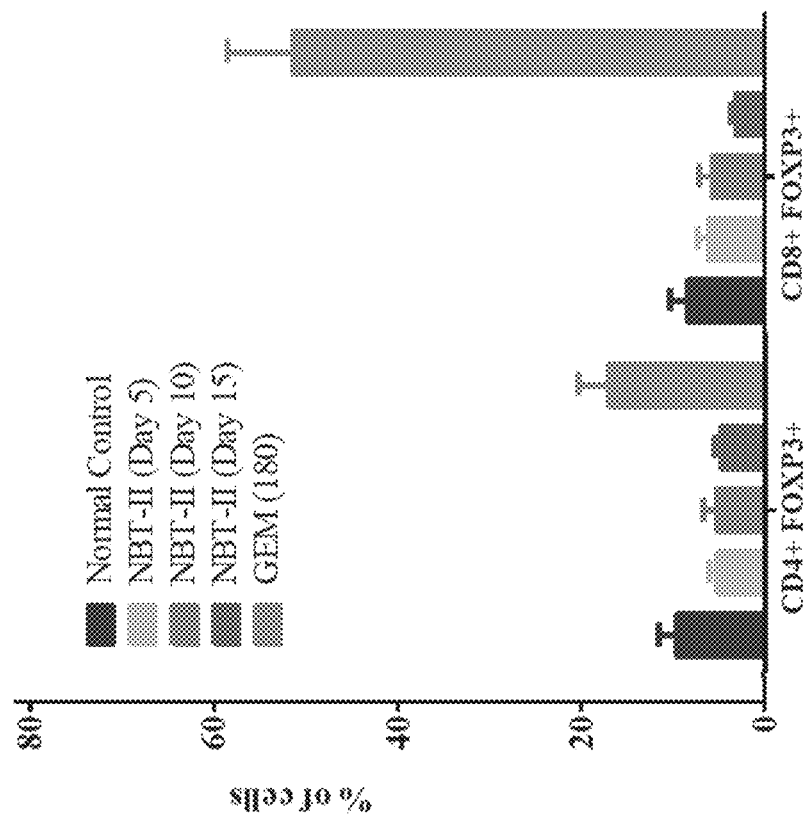
FIG. 12 shows FOXP3 splenic regulatory cell populations in tumor bearing rats administered intravesicular gemcitabine.

The percentage splenic of regulatory T cells was assed using flow cytometry. As shown in FIG. 12, rats that were inoculated with NBT-II tumors and did not receive intravesicular gemcitabine showed a decrease in both CD4+FOXP3+ and CD8+FOXP3+ regulatory T cells. Intravesicular gemcitabine increased the percentage of activated Cn both CD4+FOXP3+ and CD8+FOXP3+ regulatory T cells, thus indicating activation of the systemic immune system against the tumor.

The invention claimed is:

1. A method of treating or suppressing tumor metastasis at a site distinct from the bladder in an individual having a urothelial carcinoma of lower tract, comprising locally delivering to the bladder an effective amount of a chemotherapeutic agent, wherein the chemotherapeutic agent is delivered continuously to the bladder for at least about 24 hours.

2. The method of claim 1, wherein the tumor metastatic site is at one or more of: liver, lung, bone, brain, lymph node, peritoneum, skin, prostate, breast, colon, rectum, and cervix.

3. The method of claim 1, wherein the tumor metastasis is at two or more different sites.

4. A method of inhibiting tumor cell growth at a second tumor site distinct from a first tumor site in the bladder of an individual, comprising locally delivering to the bladder an effective amount of a chemotherapeutic agent, wherein the chemotherapeutic agent is delivered continuously to the bladder for at least about 24 hours.

5. The method of claim 4, wherein the tumor cells at the second tumor site are located at a pelvic node.

6. The method of claim 4, wherein the tumor cells at the second tumor site are located at a lymph node.

7. The method of claim 4, wherein the tumor cells at the second tumor site are circulating tumor cells.

8. The method claim 4, wherein the tumor cells at the first tumor site result from metastasis of a primary tumor at the second tumor site.

9. The method of claim 8, wherein the tumor cells at the second site are selected from the group consisting of liver, lung, bone, brain, lymph node, pelvic node, peritoneum, skin, prostate, breast, colon, rectum, and cervix.

10. The method of claim 4, wherein the individual has a urothelial carcinoma of lower tract.

11. The method of claim 4, wherein the individual has bladder cancer.

12. The method of claim 11, wherein the individual has muscle invasive bladder cancer or carcinoma in situ (CIS).

13. The method of claim 11, wherein the individual is unfit for or refuses cystectomy.

14. The method of claim 11, wherein the individual has not undergone transurethral resection of bladder tumors (TURBT).

15. The method of claim 11, wherein the individual has undergone transurethral resection of bladder tumors (TURBT).

16. The method of claim 15, wherein the individual has residual tumor at the site of resection.

17. The method of claim 4, wherein the chemotherapeutic agent is delivered continuously to the bladder of the individual for a period of about 7 days to about three weeks.

18. The method of claim 4, wherein the method comprises an induction delivery period followed by a maintenance delivery period.

19. The method of claim 18, wherein the induction delivery period and the maintenance delivery period are separated by a rest period of about 7 to about 14 days.

20. The method of claim 4, wherein the chemotherapeutic agent is delivered at a dose of from about 1 mg/day to about 300 mg/day.

21. The method of claim 4, wherein the concentration of the chemotherapeutic agent in the urine is from about 0.1 μg/mL to about 200 μg/mL during the delivery period.

22. The method of claim 4, comprising an induction delivery period, wherein the concentration of chemotherapeutic agent in the urine of the individual is at least about 0.1 μg/mL;
a rest period; and
a maintenance delivery period, wherein the concentration of the chemotherapeutic agent in the urine of the individual is greater than about 0.1 μg/mL.

23. The method of claim 4, wherein the individual does not receive a radiation therapy.

24. The method of claim 4, wherein the method further comprises a radiation therapy.

25. The method of claim 4, wherein the chemotherapeutic agent is delivered by an intravesical delivery device.

26. The method of claim 25, wherein the intravesical device contains 100 mg to 500 mg of the chemotherapeutic agent.

27. The method of claim 26, wherein the intravesical device comprises a housing configured for intravesical insertion; and a dosage form comprising chemotherapeutic agent, wherein the housing holds the dosage form and is configured to release chemotherapeutic agent.

28. The method of claim 26, wherein the intravesical drug delivery device comprises:
a housing defining a reservoir;
a first unit contained within the reservoir, the first unit comprising an chemotherapeutic agent; and
a second unit contained within the reservoir in a position distinct from the first unit, wherein the second unit comprises a functional agent that facilitates in vivo release of the chemotherapeutic agent from the housing.

29. The method of claim 28, wherein the chemotherapeutic agent contained in the housing is in a non-liquid form.

30. The method of claim 29, wherein the non-liquid form is selected from the group consisting of tablets, granules, powders, semisolids, capsules, and combinations thereof.

31. The method of claim 25, wherein the intravesical drug delivery device comprises a housing which contains and controllably releases the chemotherapeutic agent and is elastically deformable between a retention shape configured to retain the device in the individual's bladder and a deployment shape for passage of the device through the individual's urethra.

32. The method of claim 25, wherein the device comprises a drug reservoir lumen bounded by a first wall and a second wall, wherein the first wall is impermeable to the drug and the second wall is permeable to the chemotherapeutic agent.

33. The method of claim 25, wherein the chemotherapeutic agent is released from the device by osmotic pressure.

34. The method of claim 25, wherein the chemotherapeutic agent is released from the device by diffusion.

35. The method of claim 4, wherein the chemotherapeutic agent is selected from the group consisting of a nucleoside analog, a taxane, a platinum-based agent, and an anthracycline analogue.

36. The method of claim 4, wherein the chemotherapeutic agent is a nucleoside analog.

37. The method of claim 36, wherein the nucleoside analog is gemcitabine.

38. The method of claim 4, wherein the individual is human.

39. The method of claim 4, wherein the individual is unsuitable for systemic chemotherapy.

40. The method of claim 4 wherein the individual has a compromised immune system.

41. The method of claim 4, wherein the individual has a high tumor burden.

* * * * *

UNITED STATES PATENT AND TRADEMARK OFFICE
CERTIFICATE OF CORRECTION

PATENT NO. : 10,857,173 B2
APPLICATION NO. : 16/045586
DATED : December 8, 2020
INVENTOR(S) : Dennis Giesing Page 1 of 1

It is certified that error appears in the above-identified patent and that said Letters Patent is hereby corrected as shown below:

On the Title Page
On page 2 [(56) References Cited]:
At left column, in listed reference "Lorenzo, G.D. et al. (Apr. 15, 2010)", Delete ""Genncitabine" and insert --Gemcitabine--
At left column, in listed reference "Lorenzo, G.D. et al. (Apr. 15, 2010)", Delete "Gue'rin" and insert --Guerin--

In the Specification
At Column 9, Line number 5, Delete "pappilary," and insert --papillary,--
At Column 9, Line number 8, Delete "micropappliary" and insert --micropapillary--
At Column 9, Line number 8-9, Delete "lymphopithelial" and insert --lymphoepithelial--
At Column 9, Line number 12, Delete "pappilary" and insert --papillary--
At Column 22, Line number 6, Delete "pappilary," and insert --papillary,--
At Column 22, Line number 9, Delete "micropappliary" and insert --micropapillary--
At Column 22, Line number 9-10, Delete "lymphopithelial" and insert --lymphoepithelial--
At Column 22, Line number 13, Delete "pappilary" and insert --papillary--
At Column 23, Line number 37, Delete "INFγ" and insert --IFNγ--
At Column 29, Line number 23, Delete "pyrolidones)," and insert --pyrrolidones),--
At Column 30, Line number 6, Delete "formulatory" and insert --formulary--

In the Claims
At Column 48, Claim number 8, Line number 33, after "method" insert --of--

Signed and Sealed this
First Day of June, 2021

Drew Hirshfeld
*Performing the Functions and Duties of the
Under Secretary of Commerce for Intellectual Property and
Director of the United States Patent and Trademark Office*